(12) United States Patent
Inokawa et al.

(10) Patent No.: US 10,168,277 B2
(45) Date of Patent: Jan. 1, 2019

(54) REFRACTIVE INDEX MEASURING DEVICE

(71) Applicant: NATIONAL UNIVERSITY CORPORATION SHIZUOKA UNIVERSITY, Shizuoka (JP)

(72) Inventors: Hiroshi Inokawa, Hamamatsu (JP); Hiroaki Satoh, Hamamatsu (JP); Atsushi Ono, Hamamatsu (JP)

(73) Assignees: NATIONAL UNIVERSITY CORPORATION SHIZUOKA UNIVERSITY (JP); YAMAHA HATSUDOKI KABUSHIKI KAISHA (JP)

( * ) Notice: Subject to any disclaimer, the term of this patent is extended or adjusted under 35 U.S.C. 154(b) by 0 days.

(21) Appl. No.: 15/551,192

(22) PCT Filed: Feb. 10, 2016

(86) PCT No.: PCT/JP2016/053981
§ 371 (c)(1),
(2) Date: Aug. 15, 2017

(87) PCT Pub. No.: WO2016/132991
PCT Pub. Date: Aug. 25, 2016

(65) Prior Publication Data
US 2018/0011013 A1 Jan. 11, 2018

(30) Foreign Application Priority Data
Feb. 16, 2015 (JP) ................... 2015-027772

(51) Int. Cl.
*G01N 21/41* (2006.01)
*G01N 21/77* (2006.01)

(52) U.S. Cl.
CPC ......... *G01N 21/41* (2013.01); *G01N 21/4133* (2013.01); *G01N 21/7743* (2013.01);
(Continued)

(58) Field of Classification Search
CPC .. G01N 21/41; G01N 21/4133; G01N 21/431; G01N 21/43; G01N 21/552
(Continued)

(56) References Cited

U.S. PATENT DOCUMENTS

| | | | |
|---|---|---|---|
| 6,677,601 B2 * | 1/2004 | Shiraishi ................... | G03F 9/70 250/237 G |
| 7,109,508 B2 * | 9/2006 | Shiraishi ................... | G03F 9/70 250/548 |

(Continued)

FOREIGN PATENT DOCUMENTS

| | | |
|---|---|---|
| JP | 2003-28774 A | 1/2003 |
| JP | 2004-170095 A | 6/2004 |

(Continued)

OTHER PUBLICATIONS

Notification of Transmittal of Translation of the International Preliminary Report on Patentability (Chapter I or Chapter II) for PCT/JP2016/053981 dated Aug. 17, 2017.
(Continued)

*Primary Examiner* — Md M Rahman
(74) *Attorney, Agent, or Firm* — Ostrolenk Faber LLP

(57) ABSTRACT

A photodiode includes semiconductor layers and a gate insulating layer provided on a buried insulating layer formed on a substrate and has a diffraction grating portion in which a plurality of groove portions are formed in a two-dimensional lattice shape, on the gate insulating layer. Measurement light is guided by an optical system including a photoelastic modulator and is incident on the photodiode. The measurement light is emitted from the light source device in a state of being linearly polarized light having a predetermined wavelength and is converted at a predetermined frequency by the optical system such that states in which the measurement light becomes linearly polarized light beams of two orthogonal directions are repeated. In
(Continued)

addition, electric signals from the photodiode in the state in which the measurement light becomes the linearly polarized light beams of the two orthogonal directions are lock-in detected.

10 Claims, 21 Drawing Sheets

(52) U.S. Cl.
CPC ............ *G01N 2021/4166* (2013.01); *G01N 2201/061* (2013.01)

(58) Field of Classification Search
USPC ........................................................ 356/128
See application file for complete search history.

(56) References Cited

U.S. PATENT DOCUMENTS

| | | | |
|---|---|---|---|
| 2001/0030299 A1* | 10/2001 | Shiraishi | G03F 9/70 250/559.29 |
| 2005/0051742 A1* | 3/2005 | Shiraishi | G03F 9/70 250/548 |
| 2009/0134486 A1* | 5/2009 | Fujikata | H01L 31/022408 257/449 |

FOREIGN PATENT DOCUMENTS

| | | |
|---|---|---|
| JP | 2005-156414 A | 6/2005 |
| JP | 2009-168469 A | 7/2009 |
| JP | 2010-210384 A | 9/2010 |
| JP | 2011-209097 A | 10/2011 |
| JP | 2014-173920 A | 9/2014 |

OTHER PUBLICATIONS

International Search Report for corresponding International Application No. PCT/JP2016/053981 dated May 10, 2016.
Hiroaki Satoh et al., "Sensitivity Improvement in Refractive Index Measurement by Photodiode with Surface Plasmon Antenna", IEICE Technical Report, Jan. 29, 2015, vol. 114, No. 442, p. 23-p. 27.

* cited by examiner (a)

(b)

(a)

(b)

REFRACTIVE INDEX MEASURING DEVICE

CROSS-REFERENCE TO RELATED APPLICATIONS

The present application is a 35 U.S.C. §§ 371 national phase conversion of PCT/JP2016/053981, filed Feb. 10, 2016, which claims priority to Japanese Patent Application No. 2015-027772, filed Feb. 16, 2015, the contents of both of which are incorporated herein by reference. The PCT International Application was published in the Japanese language.

TECHNICAL FIELD

The present invention relates to a refractive index measuring device.

BACKGROUND ART

The measurement of a refractive index is expected to be applied in various fields such as agriculture, chemistry, biology, biotechnology, and medicine. As technology for measuring the refractive index, a measuring device and a measuring method of the refractive index using waveguide mode resonance and surface plasmon resonance are described in Patent Literatures 1 to 3.

A refractive index meter that acquires a refractive index of a sample easily with high accuracy is described in Patent Literature 1. When the refractive index is measured using the refractive index meter, measurement light is introduced into an end face of a waveguide layer of a waveguide mode resonance filter and emission light diffracted by a grating of the waveguide mode resonance filter at this time is detected by a light detector. An emission angle of the measurement light is scanned in a predetermined angle range by moving a position of the detector. As a result, a resonance emission angle corresponding to the refractive index is acquired.

A surface plasmon resonance sensor chip that has a diffraction grating and is suitable for miniaturization is described in Patent Literature 2. The diffraction grating is formed on an elastic film to be elastically deformable. When a refractive index is measured using the chip, light is incident on the diffraction grating in a state in which a sample is disposed in the vicinity of a diffraction grating surface. In a conventional surface plasmon resonance sensor chip, the intensity of diffraction light is measured by scanning an incidence angle of the incidence light. Meanwhile, in the chip, a resonance pitch corresponding to the refractive index is acquired by expanding the elastic film and changing a grating pitch of the diffraction grating surface dynamically, instead of scanning the incidence angle of the incidence light.

A surface plasmon resonance sensor is described in Patent Literature 3. The sensor has a waveguide core layer on which light for measurement is incident, a metal thin film, a dielectric film, and a sample layer to provide a sample for measurement formed on the dielectric film. When a refractive index is measured using the sensor, the sample is provided on the sample layer, light is caused to be incident on the waveguide core layer, and a wavelength spectrum or an incidence angle spectrum of the light transmitting the waveguide core layer is measured.

CITATION LIST

Patent Literature

Patent Literature 1: Japanese Unexamined Patent Publication No. 2010-210384

Patent Literature 2: Japanese Unexamined Patent Publication No. 2009-168469

Patent Literature 3: Japanese Unexamined Patent Publication No. 2004-170095

SUMMARY OF INVENTION

Technical Problem

In the refractive index measuring devices described in Patent Literatures 1 to 3, a resonance angle, a resonance wavelength, or a resonance pitch giving a resonance peak is measured on the basis of the intensity of the light emitted from the resonance filter and a refractive index is calculated from a measurement result. However, according to this method, it is necessary to provide the light detector separated from the resonance filter to detect the intensity of the light emitted from the resonance filter and a device configuration is complicated. In addition, because the light detector is provided separately, use efficiency of reflection light emitted from the resonance filter is deteriorated and detection accuracy of the intensity of the light is deteriorated, so that measurement accuracy of the refractive index tends to be deteriorated.

Accordingly, an object of one aspect of the present invention is to provide a refractive index measuring device capable of simplifying a device configuration and improving measurement accuracy of a refractive index.

Solution to Problem

A refractive index measuring device according to one aspect of the present invention includes: a photodiode configured to have a substrate made of a semiconductor or a metal, a buried insulating layer formed on the substrate, a semiconductor layer including a p-type semiconductor layer and an n-type semiconductor layer formed to be arranged along a predetermined region on the buried insulating layer, a gate insulating layer formed on the semiconductor layer, and a diffraction grating portion disposed on the gate insulating layer and having groove portions formed two-dimensionally in a planar conductive member; a light source configured to emit linearly polarized light having a predetermined wavelength; an optical system configured to include a photoelastic modulator, convert the light such that states in which the light becomes linearly polarized light beams of two orthogonal directions are repeated at a predetermined frequency, and guide the converted light to the photodiode; and a signal detection unit configured to perform lock-in detection on electric signals output from the photodiode when the light is incident on the photodiode through the optical system, at the predetermined frequency at each time when the light becomes the linearly polarized light beams of the two orthogonal directions.

The refractive index measuring device includes the semiconductor layer and the gate insulating layer that are provided on the buried insulating layer formed on the substrate. In addition, in the refractive index measuring device, the light emitted from the light source is guided by the optical system and is incident on the photodiode having the diffraction grating portion in which the groove portions are formed two-dimensionally, on the gate insulating layer. Here, the light emitted from the light source is in a state of being the linearly polarized light having the predetermined wavelength and the light incident on the photodiode is converted at the predetermined frequency by the photoelastic modulator included in the optical system, such that states in which the light incident on the photodiode becomes the linearly polarized light beams of the two orthogonal directions are repeated. In addition, the linearly polarized light beams of the two orthogonal directions are repeatedly incident on the diffraction grating portion in which the groove portions are formed two-dimensionally and each electric signal of the photodiode in states in which the light becomes the linearly polarized light beam of each direction is detected. As a result, when a measured object is disposed on the diffraction grating portion, a refractive index of the measured object can be obtained on the basis of each electric signal. By this configuration, because the refractive index can be measured without using a separate light detector, a device configuration can be simplified. In addition, use efficiency of the light incident on the photodiode is improved, so that detection accuracy of the intensity of the light is improved. In addition, the light is incident on the same measured object from the same light source and optical system and the light is converted into the electric signal by the same diffraction grating portion and photodiode, so that an error is suppressed from occurring in the electric signal. In addition, the electric signal is lock-in detected in the signal detection unit, so that a signal-to-noise (S/N) ratio is improved. As a result, measurement accuracy of the refractive index of the measured object can be improved.

Advantageous Effects of Invention

According to one aspect of the present invention, a device configuration can be simplified and measurement accuracy of a refractive index can be improved.

DESCRIPTION OF EMBODIMENTS

Figure 1:
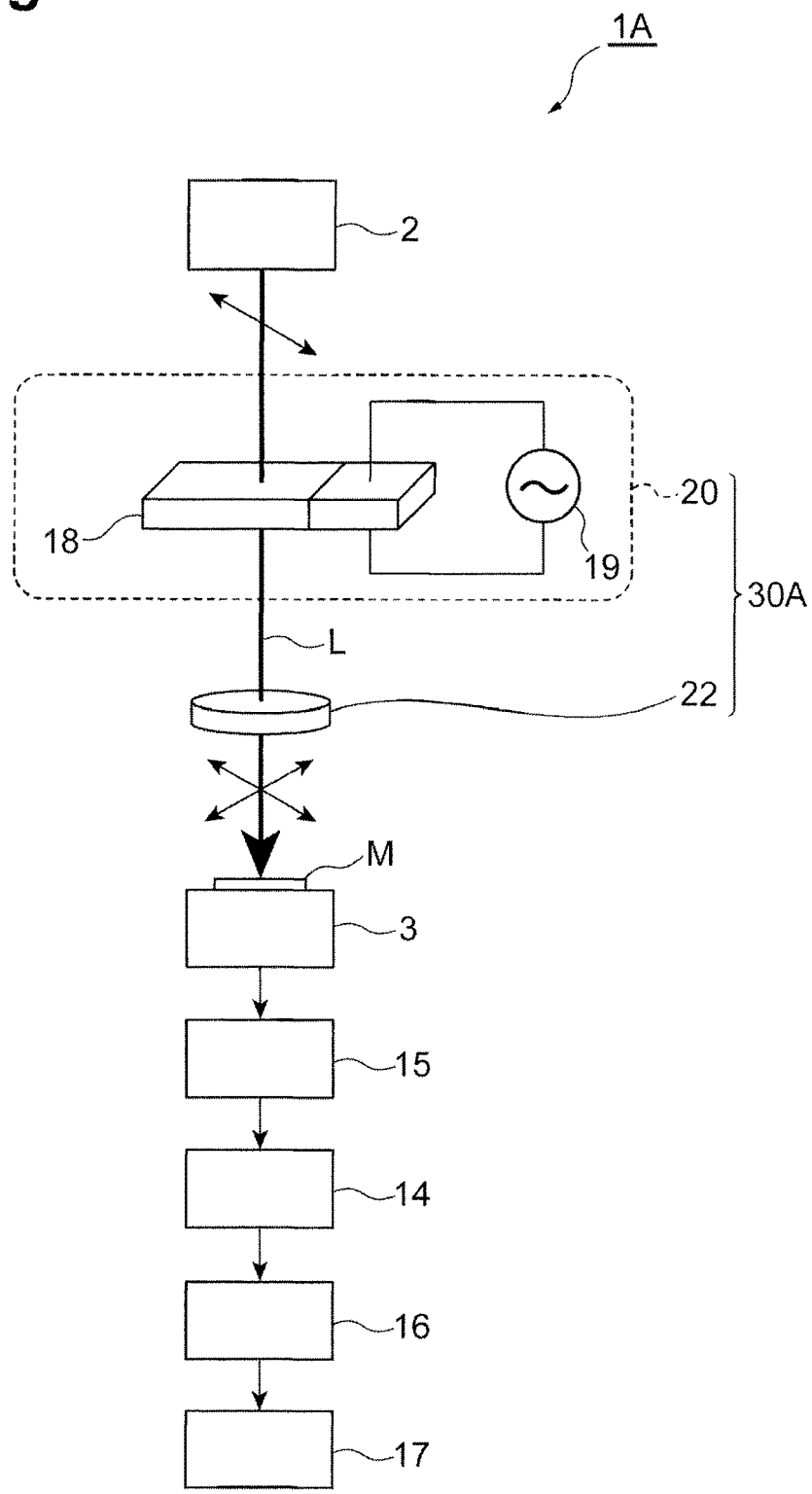
FIG. 1 is a schematic configuration diagram showing a refractive index measuring device according to a first embodiment.

Hereinafter, embodiments for carrying out the present invention will be described in detail with reference to the accompanying drawings. In the description of the drawings, the same elements are denoted by the same reference numerals and duplicate explanation is omitted.

(First Embodiment)

FIG. 1 is a schematic configuration diagram showing a refractive index measuring device according to a first embodiment. As shown in FIG. 1, a refractive index measuring device 1A according to this embodiment is a device that obtains a refractive index n of a measured object M by radiating measurement light (light) L to the measured object M. The refractive index measuring device 1A includes a photodiode 3 that outputs an electric signal according to the refractive index n of the measured object M disposed, by the radiation of the measurement light L, a light source device (light source) 2 that emits the measurement light L, and an optical system 30A that converts a polarization state of the measurement light L emitted from the light source device 2 and guides the measurement light L to the photodiode 3. Further, the refractive index measuring device 1A includes, as a configuration for processing and detecting the electric signal output from the photodiode 3, a logarithmic conversion circuit 15 logarithmically converting the electric signal, a sample/hold circuit 14 sampling/holding the electric signal output from the logarithmic conversion circuit 15, a signal detection unit 16 performing lock-in detection on the electric signal output from the sample/hold circuit 14, and a refractive index calculation unit 17 calculating the refractive index n of the measured object M, on the basis of the electric signal lock-in detected by the signal detection unit 16.

First, a configuration of the photodiode 3 will be described.

Figure 2:
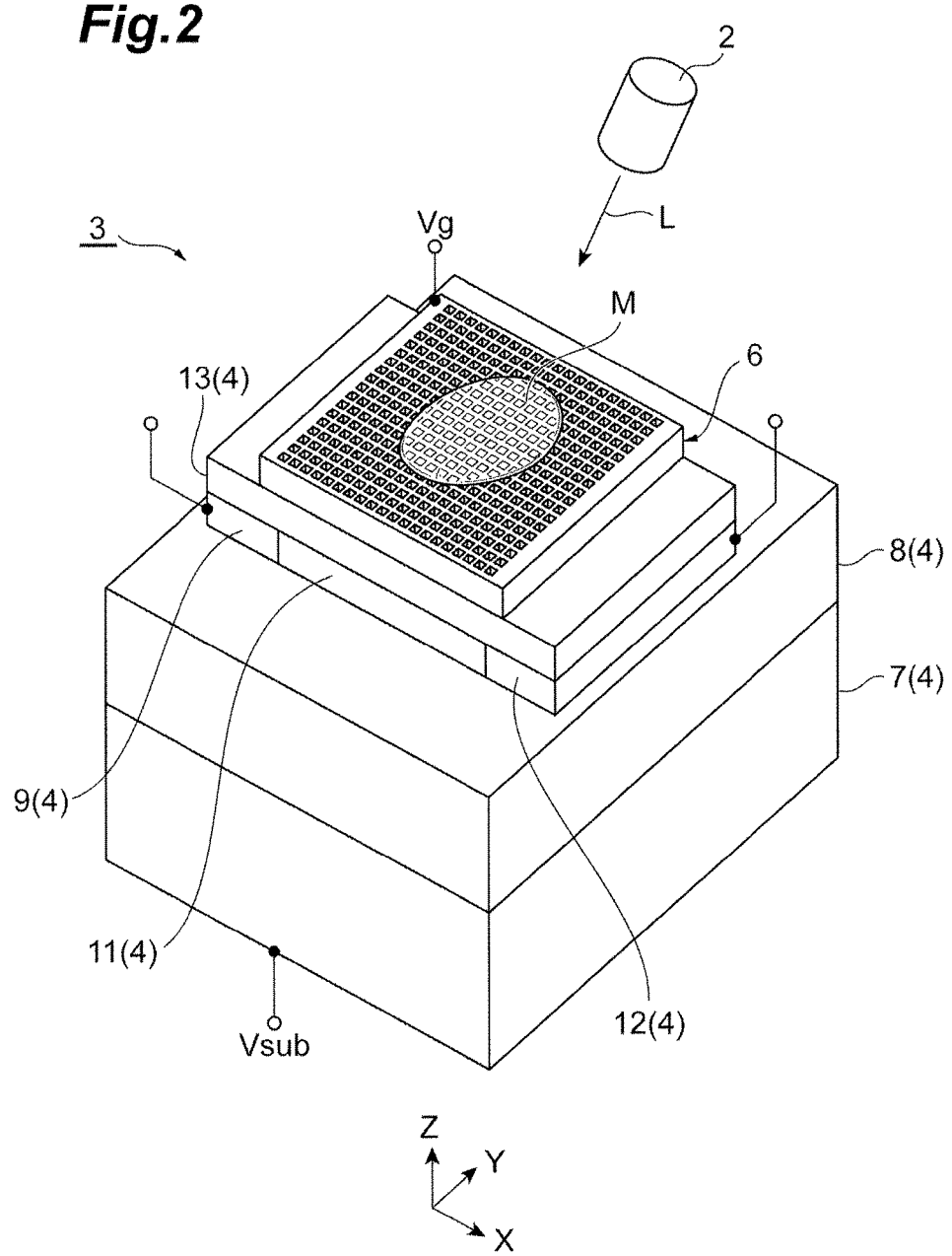
FIG. 2 is a perspective view showing a photodiode used in the refractive index measuring device.
Figure 3:
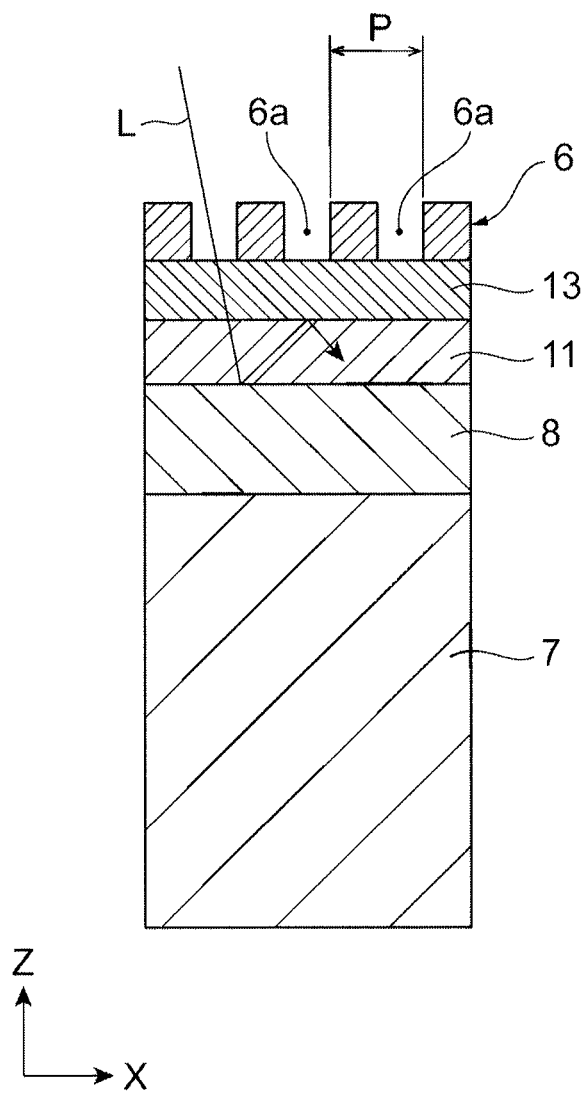
FIG. 3 is a cross-sectional view of a main portion of the photodiode.

FIG. 2 is a perspective view showing the photodiode used in the refractive index measuring device and FIG. 3 is a cross-sectional view of a main portion of the photodiode. As shown in FIGS. 2 and 3, the photodiode 3 includes a semiconductor light reception element unit 4 that generates an electric signal corresponding to light intensity of measurement light L and a diffraction grating portion 6 that is provided on the semiconductor light reception element unit 4. In the following description, it is assumed that a lamination direction of individual layers configuring the photodiode 3 is a Z-axis direction, arrangement directions of a plurality of groove portions 6a formed in a two-dimensional lattice shape in the diffraction grating portion 6 to be described below are an X-axis direction and a Y-axis direction, and individual axes are orthogonal to each other.

The semiconductor light reception element unit 4 of the photodiode 3 is a lateral pn junction diode of a so-called MOS structure and has a silicon substrate (substrate) 7, a buried insulating layer 8 disposed on the silicon substrate 7, semiconductor layers 9, 11, and 12 disposed on the buried insulating layer 8, and a gate insulating layer 13 disposed on the semiconductor layers 9, 11, and 12. The buried insulating layer 8 is made of silicon oxide, the semiconductor layers 9, 11, and 12 are made of silicon containing a predetermined dopant, and the gate insulating layer 13 is made of silicon oxide. Therefore, the semiconductor light reception element unit 4 has a Silicon On Insulator (SOI) structure in which the silicon substrate 7 is used as a substrate (support object).

The semiconductor layers 9, 11, and 12 are provided adjacently in this order along the X-axis direction in a predetermined region of a rectangular shape on the buried insulating layer 8. In the semiconductor layer 11 functioning as an optical waveguide and a light absorption layer, a major portion in a depth direction (Z-axis direction) is depleted and p-type impurities or n-type impurities such as boron and phosphorus are added to silicon at a low concentration. The semiconductor layers 9 and 12 to be an anode electrode and a cathode electrode are formed as a p⁺-type semiconductor layer and an n⁺-type semiconductor layer, respectively, with almost the same thickness as the thickness of the semiconductor layer 11 so as to sandwich the semiconductor layer 11 from the direction along the X axis on the buried insulating layer 8. In the p⁺-type semiconductor layer 9 and the n⁺-type semiconductor layer 12, p-type impurities such as boron and n-type impurities such as phosphorus are added to silicon at a high concentration ($10^{19}$ cm⁻³ or more). The semiconductor layers 9 and 12 are provided in parallel with the semiconductor layer 11 and function as the anode electrode and the cathode electrode, respectively. The gate insulating layer 13 is formed on the semiconductor layers 9, 11, and 12 to cover the semiconductor layers 9, 11, and 12.

When the measurement light L is detected by the photodiode 3, a gate voltage Vg is applied to the diffraction grating portion 6 and a substrate voltage Vsub is applied to the silicon substrate 7. The gate voltage Vg and the substrate voltage Vsub are adjusted, so that densities of electrons or holes at upper and lower interfaces of the semiconductor layer 11 can be controlled over a wide range. Particularly, the gate voltage Vg and the substrate voltage Vsub are preferably set such that the densities of the electrons or the holes at the interface of the semiconductor layer 11 contacting the gate insulating layer 13 and the interface of the semiconductor layer 11 contacting the buried insulating layer 8 are sufficiently larger than an intrinsic carrier density of the semiconductor layer 11.

The diffraction grating portion 6 is disposed in a region covering at least the semiconductor layer 11 on the gate insulating layer 13. Therefore, the diffraction grating portion 6 covers the semiconductor layer 11 with the gate insulating layer 13 therebetween and is electrically insulated from the semiconductor layers 9, 11, and 12. In the diffraction grating portion 6, the plurality of groove portions 6a penetrating a portion up to a surface of the gate insulating layer 13 over the region covering the semiconductor layer 11 are formed in a metal film to be a planar conductive member. Each of the groove portions 6a has an opening of an approximately square shape. The plurality of groove portions 6a are arranged in the X-axis direction and the Y-axis direction and are formed in a two-dimensional lattice shape. That is, the plurality of groove portions 6a are arranged at a constant grating pitch (period) P in the X-axis direction and the Y-axis direction and the two arrangement directions of the plurality of groove portions 6a along the X-axis direction and the Y-axis direction are orthogonal to each other. As a material of the diffraction grating portion 6, for example, a conductive metal such as gold (Au), silver (Ag), and aluminum (Al) formed on an adhesion strengthening layer of titanium (Ti) and polycrystalline silicon (poly Si) containing n-type or p-type impurities added at high concentration are used. The diffraction grating portion 6 has a function of guiding the measurement light L having a predetermined wavelength to the semiconductor layer 11, a function as a gate electrode, and a function as an arrangement portion to arrange the measured object M.

In the photodiode 3, if the measurement light L is radiated to the diffraction grating portion 6, the measurement light L of a specific wavelength satisfying a phase matching condition with a waveguide mode of the semiconductor layer 11 is most efficiently captured in the semiconductor layer 11. The measurement light L captured in the semiconductor layer 11 is absorbed into the semiconductor layer 11 and generates electron/hole pairs. In addition, because a photocurrent corresponding to an amount of generated and separated electrons and holes flows from the cathode to the anode, an electric signal is extracted from the semiconductor layer 12.

A propagation wavelength $\lambda_g$ of the waveguide mode in the semiconductor layer 11 is represented by Formula (1). Here, $\lambda$ shows a wavelength of the measurement light L, $n_s$ shows a refractive index of the semiconductor layer 11, $t_s$ shows a thickness of the semiconductor layer 11, and $n_i$ shows a refractive index of each of the buried insulating layer 8 and the gate insulating layer 13. A TE mode is a mode in which an electric field direction of light propagating through the waveguide (that is, the semiconductor layer 11) is vertical to a propagation direction and is in a waveguide plane. Likewise, a TM mode is a mode in which the electric field direction is vertical to the propagation direction and is in the waveguide plane. Formula (1) is different according to each mode.

[Formula 1]

$$\left.\begin{aligned}\tan\left(\frac{ht_s}{2} - m\frac{\pi}{2}\right) &= \frac{\sqrt{V^2 - h^2 t_s^2}}{ht_s} \quad \ldots \text{ TE mode} \\ \tan\left(\frac{ht_s}{2} - m\frac{\pi}{2}\right) &= \frac{n_s^2}{n_i^2}\frac{\sqrt{V^2 - h^2 t_s^2}}{ht_s} \quad \ldots \text{ TM mode}\end{aligned}\right\} \quad (1)$$

provided that $h = \sqrt{\left(\frac{2\pi n_s}{\lambda}\right)^2 - \left(\frac{2\pi}{\lambda_g}\right)^2}$ $V = \frac{2\pi}{\lambda} t_s \sqrt{n_s^2 - n_i^2}$ $m$ = integer of 0, 1, 2, 3 ...

Figure 4:
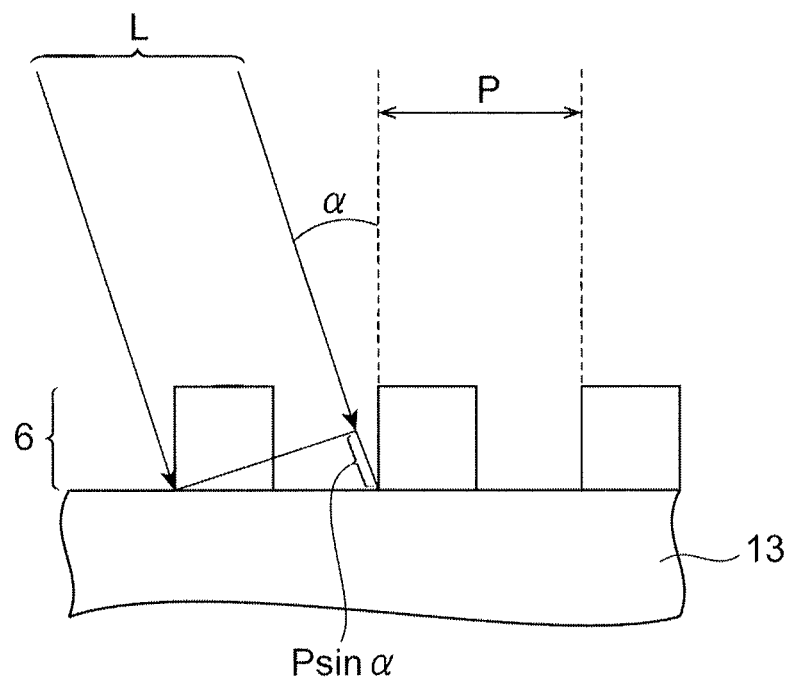
FIG. 4 is a diagram showing a relation of a phase matching condition of measurement light and a waveguide mode.
Figure 4:
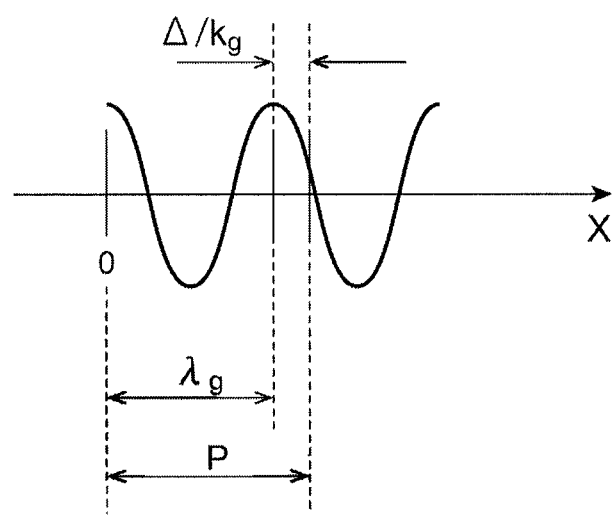

The phase matching condition will be described. FIG. 4 is a diagram showing the phase matching condition of the measurement light and the waveguide mode and shows a cross-section vertical to the Y axis. As shown in FIG. 4(a), when the measurement light L is obliquely incident on the diffraction grating portion 6 at an incidence angle α, a phase difference Δ (=P(2πn/λ)sin α) occurs due to an optical path length (P×sin α) generated per pitch in the diffraction grating portion 6, a refractive index n, and a wavelength λ. In addition, the phase matching condition shows that a value (=λ_g±Δ/k_g) obtained by adding or subtracting a value (Δ/k_g) obtained by dividing the phase difference Δ by a wave number k_g (=2π/λ_g) with respect to the propagation wavelength λ_g of the semiconductor layer 11 is equal to a grating pitch P. FIG. 4(b) shows the case of the addition and a forward wave propagates through the semiconductor layer 11. In the case of the subtraction, a backward wave propagates through the semiconductor layer 11. Therefore, Formulae (2-1) and (2-2) are obtained. Here, λ shows a wavelength of the measurement light L, n shows a refractive index of the measured object M, P shows a grating pitch, and a shows an incidence angle of the measurement light L. In addition, $\lambda_{gf}$ shows a propagation wavelength of the forward wave in the semiconductor layer 11 and $\lambda_{gb}$ shows a propagation wavelength of the backward wave in the semiconductor layer 11. The case in which the phase matching condition is satisfied is the case in which Formulae (2-1) and (2-2) are satisfied. According to Formulae (2-1) and (2-2), the case in which the phase matching condition is satisfied also refers to the case in which values defined by the grating pitch P, the refractive index n, the wavelength λ of the measurement light L, and the incidence angle α are matched with the propagation wavelengths $\lambda_{gf}$ and $\lambda_{gb}$ of the waveguide mode.

[Formula 2]

$$\lambda_{gf}=1/\{(1/P)+(n/\lambda)\sin \alpha\} \quad (2\text{-}1)$$

$$\lambda_{gb}=1/\{(1/P)-(n/\lambda)\sin \alpha\} \quad (2\text{-}2)$$

According to Formulae (2-1) and (2-2), it can be seen that, if the refractive index n changes in a state in which the incidence angle α of the measurement light L is other than 0 degree, that is, the measurement light L is obliquely radiated to the diffraction grating portion 6, it is necessary to shift the wavelength λ of the measurement light L to satisfy the phase matching condition.

Figure 5:
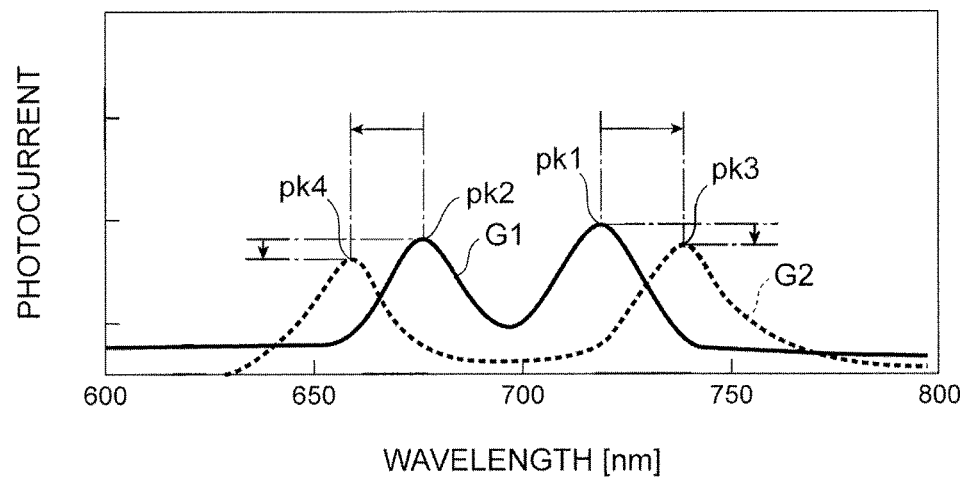
FIG. 5 is a graph showing a relation of a refractive index and a peak wavelength and a peak value.
Figure 5:
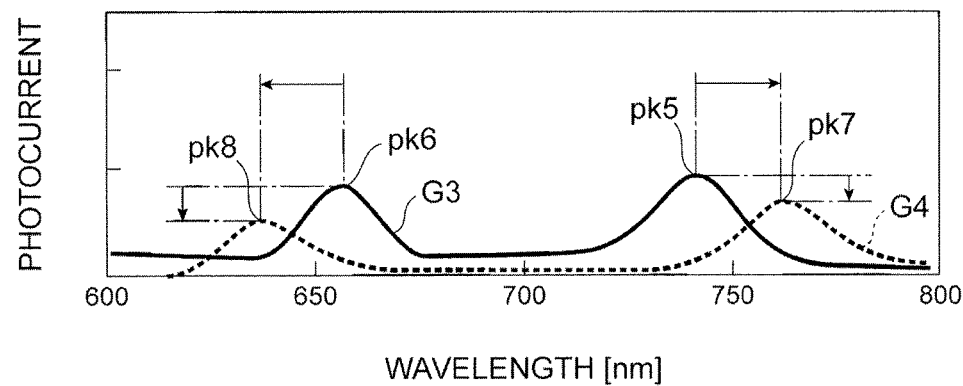

A spectral characteristic of the photocurrent will be described. FIG. 5 is a graph showing a relation of a refractive index and a peak wavelength and a peak value. As shown in FIG. 5, the spectral characteristic of the photocurrent is a relation of the wavelength λ of the measurement light L and the magnitude of an electric signal output from the photodiode 3 when the measurement light L is radiated. The spectral characteristic of the photocurrent shows the magnitude of the electric signal for each wavelength λ. In FIG. 5, a horizontal axis shows the wavelength λ of the measurement light L and a vertical axis shows the photocurrent showing the magnitude of the electric signal. When values of right sides of Formulae (2-1) and (2-2) approximate the propagation wavelengths $\lambda_{gf}$ and $\lambda_{gb}$ of the left sides, a value of the electric signal increases. In addition, when the values of the right sides and the values of the left sides are matched (when the phase matching condition is satisfied), the electric signal becomes a maximum value (peak). Efficiency (that is, quantum efficiency) at which the measurement light entering the photodiode 3 is converted into the photocurrent is obtained by dividing the photocurrent by the number of photons and the elementary electric charge entering the photodiode 3 in one second.

The shift of the peak wavelength λp according to the change in the refractive index n will be further described. FIG. 5 (a) shows a spectral characteristic of the photocurrent when the incidence angle α of the measurement light L with respect to the diffraction grating portion 6 inclined in a Z-X plane is 10 degrees. FIG. 5 (b) shows a spectral characteristic of the photocurrent when the incidence angle α of the measurement light L with respect to the diffraction grating portion 6 is 20 degrees. In addition, a graph G1 of FIG. 5(a) and a graph G3 of FIG. 5(b) show spectral characteristics of the photocurrent when the refractive index of the measured object M is n=1. The graph G1 has two peaks pk1 and pk2 and the graph G3 has peaks pk5 and pk6. In the two peaks, a long wavelength peak (that is, the peak pk1 or pk5) corresponds to a backward wave and a short wavelength peak (that is, the peak pk2 or pk6) corresponds to a forward wave. A graph G2 of FIG. 5(a) and a graph G4 of FIG. 5(b) show spectral characteristics of the photocurrent when the refractive index of the measured object M is n=1.4933. The graph G2 has two peaks pk3 and pk4 and the graph G4 has peaks pk7 and pk8. Likewise, a long wavelength peak (that is, the peak pk3 or pk7) corresponds to a backward wave and a short wavelength peak (that is, the peak pk4 or pk8) corresponds to a forward wave.

Here, it can be seen that, if the peaks pk1 and pk3 of the backward waves of FIG. 5(a) are compared, the peak wavelength λp is shifted to the long wavelength side in the peak pk3 of the graph G2 (n=1.4933), with respect to the peak pk1 of the graph G1 (n=1). In addition, it can be seen that, for the peaks of the forward waves, the peak wavelength λp is shifted to the short wavelength side in the peak pk4 of the graph G2 (n=1.4933), with respect to the peak pk2 of the graph G1 (n=1). In addition, it can be seen that, if the peaks pk1 and pk3 of FIG. 5(a) are compared, a peak value decreases in the peak pk3 of the graph G2 (n=1.4933), with respect to the peak pk1 of the graph G1 (n=1). In addition, it can be seen that a peak value decreases in the peak pk4 of the graph G2 (n=1.4933), with respect to the peak pk2 of the graph G1 (n=1).

As such, it can be seen that there is a predetermined relation between a shift amount of the peak wavelength λp and the refractive index n and there is also a predetermined relation between a decrease amount of the peak value and the refractive index n. Therefore, the refractive index n can be obtained using the shift amount of the peak wavelength λp or the decrease amount of the peak value.

Figure 6:
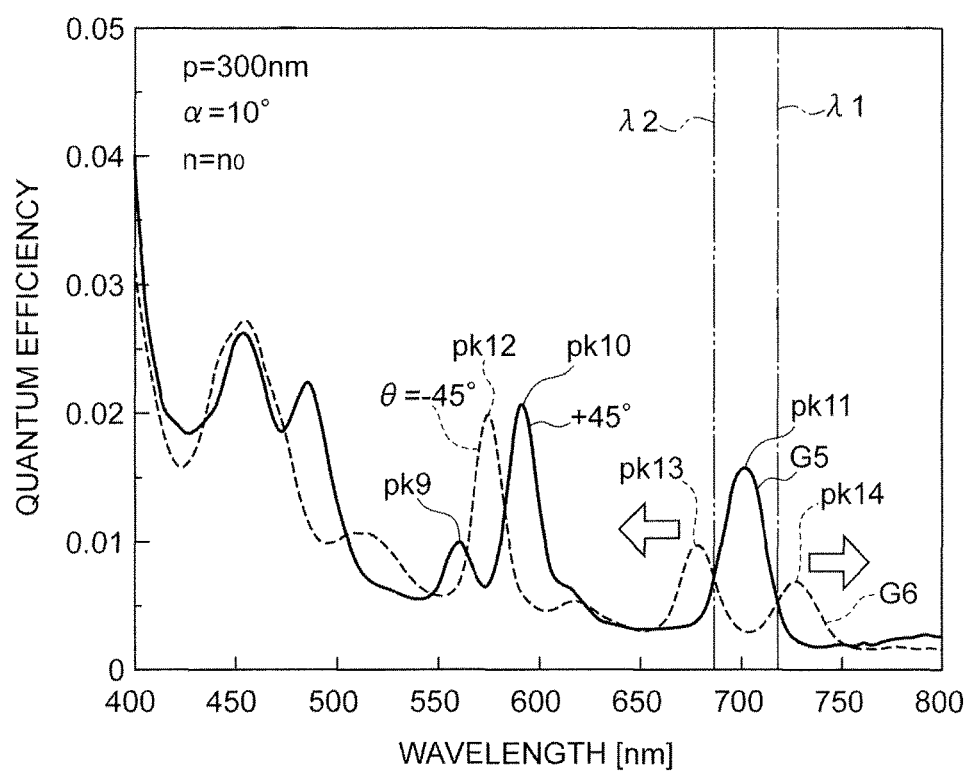
FIG. 6 is a graph showing a spectral characteristic of quantum efficiency with respect to an incidence polarization angle.

Splitting of the peak caused by the change in the polarization state of the measurement light L will be further described. FIG. 6 is a graph showing a spectral characteristic of quantum efficiency with respect to an incidence polarization angle. In FIG. 6, the spectral characteristic of the quantum efficiency when each grating pitch P of the plurality of groove portions 6a of the diffraction grating portion 6 in the X-axis direction and the Y-axis direction is 300 nm and the incidence angle α of the measurement light with respect to the diffraction grating portion 6 is 10 degrees is shown. A graph G5 shows a spectral characteristic of quantum efficiency when an oscillation direction (that is, a direction of linearly polarized light) of the electric field of the measurement light L to be the linearly polarized light is the Y-axis direction and a graph G6 shows a spectral characteristic of quantum efficiency when the oscillation direction of the electric field of the measurement light L to be the linearly polarized light is the X-axis direction. The graph G5 has peaks pk9 and pk10 corresponding to the TE mode and a peak pk11 corresponding to the TM mode and the graph G6 has a peak pk12 corresponding to the TE mode and peaks pk13 and pk14 corresponding to the TM mode, for example. For example, when the oscillation direction of the electric field of the measurement light L to be the linearly polarized light changes from the X-axis direction to the Y-axis direction, the peak pk12 of the graph G6 corresponding to the TE mode is split into two peaks having different wavelengths and becomes the peaks pk9 and pk10 of the graph G5. In addition, for example, when the oscillation direction of the electric field of the measurement light L to be the linearly polarized light changes from the Y-axis direction to the X-axis direction, the peak pk11 of the graph G5 corresponding to the TM mode is split into two peaks having different wavelengths and becomes the peaks pk13 and pk14 of the graph G6. Further, the refractive index n of the measured object M at this time is set as a reference refractive index $n_0$ and the grating pitch P and the incidence angle α are set such that quantum efficiencies (that is, electric signals by the photocurrent) with respect to the measurement light L of linearly polarized light beams of two orthogonal directions of the X-axis direction and the Y-axis direction are equalized. FIG. 6 shows that P=300 nm and α=10 degrees are set with respect to the wavelength 1 of the long wavelength side and the wavelength λ2 of the short wavelength side with respect to the peak pk11 of the TM mode.

Here, there is a predetermined relation between a width of the split peak wavelength λp and the refractive index n of the measured object M and the width of the split peak wavelength λp increases when a difference of the refractive index n and the reference refractive index no increases. For this reason, in the case in which the wavelength of the measurement light L is equalized, when the difference of the refractive index n and the reference refractive index no increases, a difference of the quantum efficiencies increases. Therefore, the difference of the quantum efficiencies is evaluated, so that the refractive index n of the measured object M can be obtained.

Next, configurations of the light source device 2 and the optical system 30A will be described.

The light source device 2 emits the measurement light L having a specific wavelength included in a predetermined band. The measurement light L is emitted in a state of linearly polarized light. In addition, the light source device 2 can adjust the incidence angle α (refer to FIG. 4 (*a*)) of the measurement light L with respect to the diffraction grating portion 6 of the photodiode 3, in cooperation with the optical system 30A. The light source device 2 and the optical system 30A are disposed such that the measurement light L travels along the Z-X plane and is incident on the diffraction grating portion 6 at the incidence angle α of 10 degrees with respect to the Z axis.

The optical system 30A converts the polarization state of the measurement light L emitted from the light source device 2 and guides the measurement light L to the photodiode 3. The optical system 30A includes a photoelastic modulator 20 having a photoelastic modulation element 18 and an AC power supply 19 and a downstream ¼ wavelength plate (¼ wavelength plate) 22 (refer to FIG. 1). The measurement light L emitted from the light source device 2 passes through the photoelastic modulation element 18 and the downstream ¼ wavelength plate 22 in this order and is incident on the photodiode 3.

The photoelastic modulator 20 converts the polarization state of the measurement light L to generate a retardation (phase difference) according to an application voltage. For example, the photoelastic modulator 20 can perform mutual conversion between linearly polarized light and circularly polarized light, conversion from linearly polarized light to linearly polarized light of a different direction, and conversion from circularly polarized light to circularly polarized light of a different rotational direction. The photoelastic modulation element 18 of the photoelastic modulator 20 is connected to the AC power supply 19. The AC power supply 19 applies, to the photoelastic modulation element 18, an AC voltage in which the photoelastic modulator 20 alternately repeats a maximum retardation of λ/4 or λ/2 with positive and negative. As such, the retardation (phase difference) changing in conjunction with a voltage change by the AC power supply 19 is generated in the measurement light L, so that the photoelastic modulator 20 periodically converts the polarization state of the measurement light L. In this embodiment, the fast axis and the slow axis of the photoelastic modulator 20 are in a state in which angles are deviated by ±45 degrees with respect to the directions of the linearly polarized light beams of the measurement light L emitted from the light source device 2.

The downstream ¼ wavelength plate 22 is made of a ¼ wavelength plate and generates the phase difference of λ/4 according to the polarization direction of the measurement light L passing through the downstream ¼ wavelength plate 22. For example, the downstream ¼ wavelength plate 22 can perform mutual conversion between the linearly polarized light and the circularly polarized light and in this embodiment, the downstream ¼ wavelength plate 22 converts the circularly polarized light into the linearly polarized light.

The sample/hold circuit 14 is a circuit to sample an output of the electric signal at a predetermined period and maintain a corresponding output value until next sampling timing, to remove unnecessary signals mixed in the electric signals output from the photodiode 3. Specifically, in the configuration of the refractive index measuring device 1A, the sample/hold circuit 14 samples/holds the output of the electric signal in synchronization with a sampling pulse synchronized with a frequency of the AC power supply 19, which is generated at timing when the retardation of the photoelastic modulator 20 becomes ±λ/4. That is, the sample/hold circuit 14 samples/holds the output of the electric signal at each time when the measurement light L becomes linearly polarized light beams of directions along the two orthogonal arrangement directions (the X-axis direction and the Y-axis direction) of the plurality of groove portions 6a in the diffraction grating portion 6.

Figure 7:
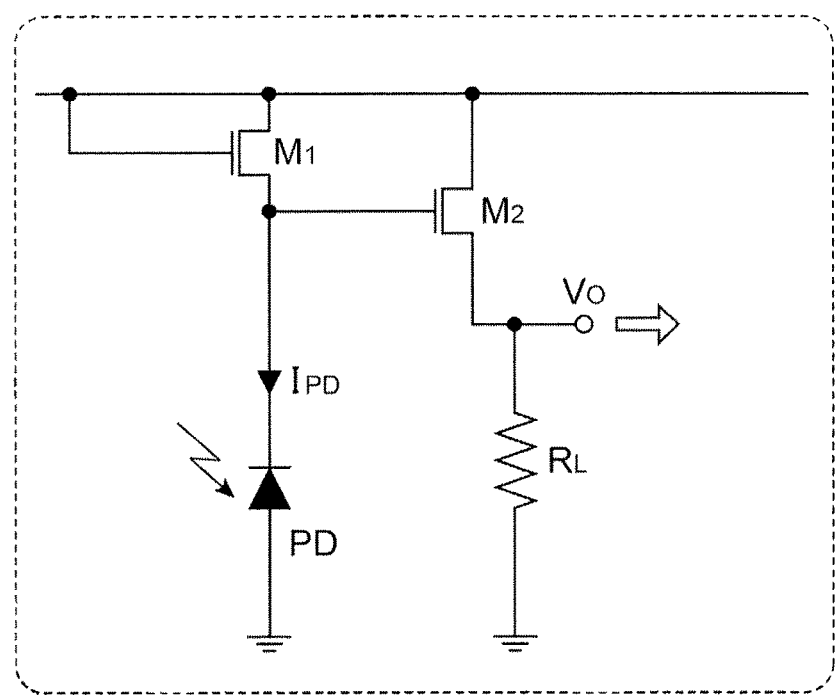
FIG. 7 is a diagram showing an example of a logarithmic conversion circuit.
Figure 8:
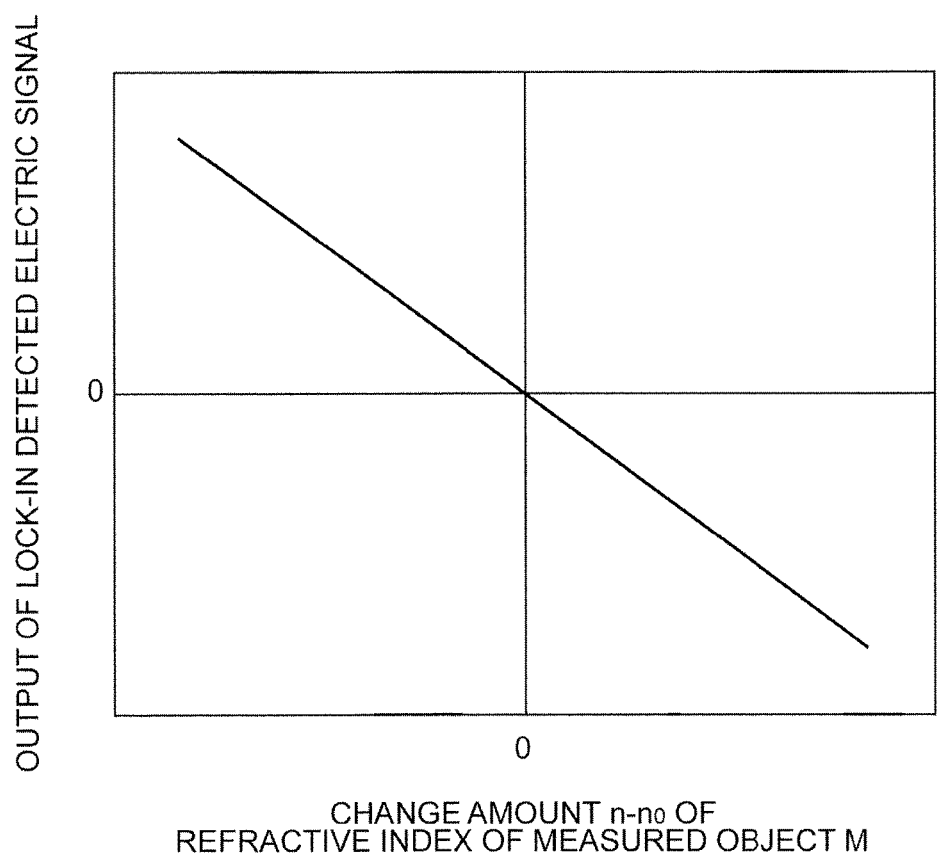
FIG. 8 is a graph showing a relation of a refractive index of a measured object and a lock-in detected output.

The logarithmic conversion circuit 15 is a circuit that logarithmically converts the electric signal output from the photodiode 3. FIG. 7 is a diagram showing an example of the logarithmic conversion circuit and FIG. 8 is a graph showing a relation of the refractive index of the measured object and the lock-in detected output. The logarithmic conversion circuit 15 is configured as shown in FIG. 7 as an example. In FIG. 7, PD shows the photodiode 3, $M_1$ shows a first MOSFET (field effect transistor), $M_2$ shows a second MOSFET, and $R_L$ shows a resistive element. In the photodiode 3, an anode is grounded and a cathode is connected to a source (current terminal) of the first MOSFET. In addition, the source of the first MOSFET is connected to a gate (control terminal) of the second MOSFET and a drain (current terminal) and a gate thereof are connected to a power supply and a voltage is applied to the first MOSFET. A source of the second MOSFET is connected to an output terminal $V_o$ and is connected to a ground via the resistive element $R_L$ and a drain thereof is connected to the power supply and a voltage is applied to the second MOSFET. An output of the logarithmic conversion circuit 15 is output from the output terminal $V_o$ to the signal detection unit 16 through the sample/hold circuit 14. As described above, the refractive index measuring device 1A is configured such that a difference of individual photocurrents $I_{PD}$ output from the photodiode 3 by incidence of the measurement light L in a state of being the linearly polarized light beams of the two orthogonal directions, on the photodiode 3, becomes 0 in the case of the reference refractive index no. In addition, as shown in FIG. 8, the difference of the individual photocurrents $I_{PD}$ changes approximately linearly in accordance with a change in the refractive index n in the vicinity of the reference refractive index $n_0$. Here, the intensity of the photocurrent $I_{PD}$ depends on the intensity of the measurement light L from the light source device 2 and when the measurement light L becomes weak, the intensity of the photocurrent $I_{PD}$ also becomes weak. For this reason, even in the case in which there is a difference of the refractive index n of the measured object M and the reference refractive index $n_0$, when the measurement light L is weak, the difference of the individual photocurrents $I_{PD}$ in a state of being the linearly polarized light beams of the two orthogonal directions is small and detection is difficult, which results in becoming one cause of deterioration of the measurement accuracy of the refractive index.

Figure 9:
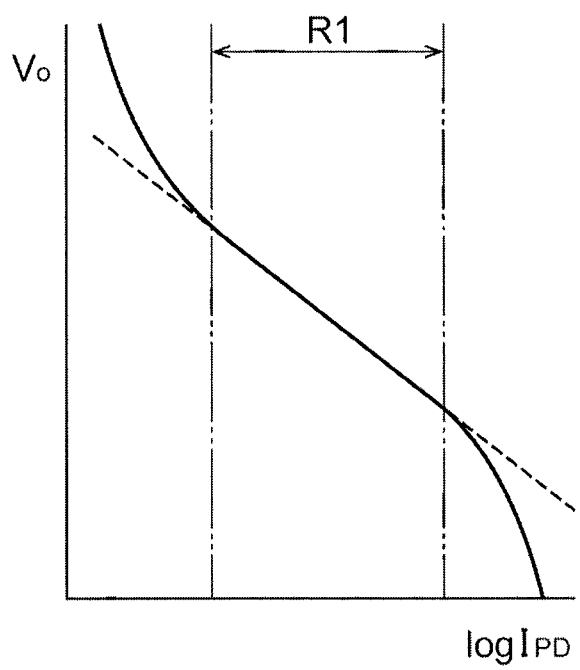
FIG. 9 is a graph showing a relation of a logarithmic value of a photocurrent and an output voltage of the logarithmic conversion circuit.

Here, a difference of individual photocurrents $\log(I_{PD})$ logarithmically converted by the logarithmic conversion circuit 15 corresponds to logarithmic conversion of a ratio of the individual photocurrents $I_{PD}$. Therefore, because the difference of the individual photocurrents $\log(I_{PD})$ does not depend on the absolute intensity of the photocurrents $I_{PD}$, the ratio of the individual photocurrents $I_{PD}$ in a state of being the linearly polarized light beams of the two orthogonal directions can be detected with high accuracy by using the difference. FIG. 9 is a graph showing a relation of a logarithmic value of the photocurrent $I_{PD}$ and an output voltage $V_0$ of the logarithmic conversion circuit. As shown in FIG. 9, in a region RI, the relation of the photocurrent $\log(I_{PD})$ and the output voltage $V_0$ can be approximated approximately linearly. Therefore, the ratio of the individual photocurrents $I_{PD}$ can be detected with the high accuracy by using the output voltage $V_0$ in the range of the region RI.

The signal detection unit 16 performs the lock-in detection on the electric signal that is output from the logarithmic conversion circuit 15 and is sampled/held by the sample/hold circuit 14. As described above, the electric signal input to the signal detection unit 16 is an electric signal output after the electric signal output from the photodiode 3 when the measurement light L is incident on the photodiode 3 through the optical system 30A passes through the logarithmic conversion circuit 15 and the sample/hold circuit 14. The signal detection unit 16 is configured to include a lock-in amplifier and detects a difference of logarithmically converted electric signals. The signal detection unit 16 is operated in synchronization with sampling pulses generated at two timings at which the retardation of the photoelastic modulator 20 becomes $\pm\lambda/4$ at a predetermined frequency (that is, individual times when the measurement light L becomes the linearly polarized light beams of the directions along the two orthogonal arrangement directions (the X-axis direction and the Y-axis direction) of the plurality of groove portions 6a in the diffraction grating portion 6). As a result, the signal detection unit 16 detects a differential voltage of electric signals at the two timings. Therefore, an influence of noise included in the electric signals can be greatly reduced. A known circuit configuration may be used as the lock-in amplifier.

The refractive index calculation unit 17 calculates the refractive index n of the measured object M, on the basis of the electric signal lock-in detected in the signal detection unit 16. As described above, the refractive index calculation unit 17 calculates the refractive index n of the measured object M by evaluating the difference of the quantum efficiencies according to the difference of the refractive index n and the reference refractive index $n_0$.

Figure 10:
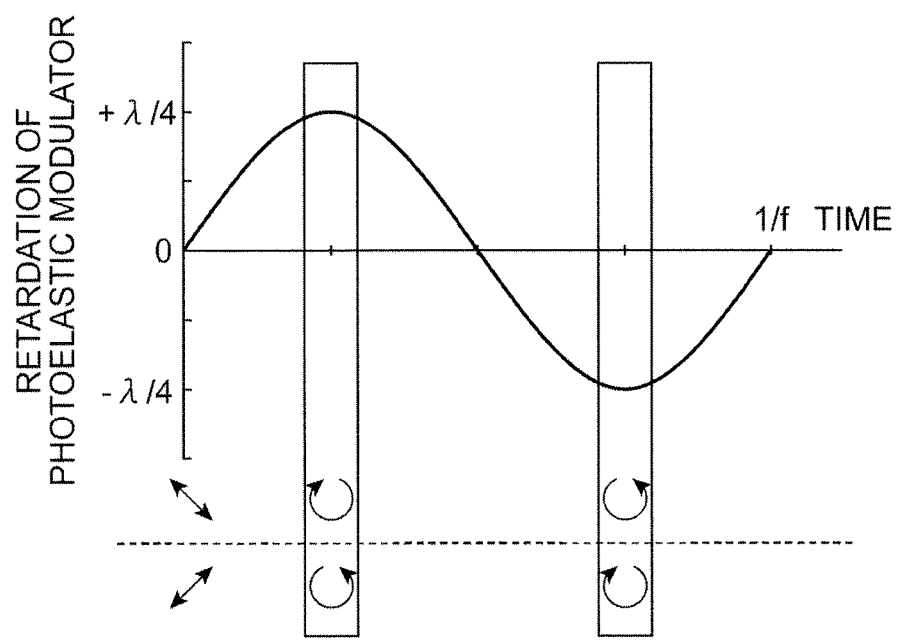
FIG. 10 is a diagram showing a temporal change of a polarization state after conversion by a photoelastic modulator in the first embodiment.

FIG. 10 is a diagram showing a temporal change of the polarization state after the conversion by the photoelastic modulator in the first embodiment. In a lower portion of FIG. 10, the polarization state after the conversion is schematically shown to correspond to two kinds of polarization states of the light incident on the photoelastic modulator 20 (hereinafter, this is applicable to FIGS. 13, 15, 17, 19, and 21). The polarization state after the conversion shown at time 0 is equal to the polarization state of the incidence light. As shown in FIG. 10, in the refractive index measuring device 1A, the measurement light L emitted from the light source device 2 is the linearly polarized light beams of the directions deviated by 45 degrees with respect to the fast axis and the slow axis of the photoelastic modulator 20. The measurement light L is converted into circularly polarized light when the measurement light L passes through the photoelastic modulator 20. The maximum retardation of the photoelastic modulator 20 is set to $\lambda/4$. When the retardation of the photoelastic modulator 20 is $\pm\lambda/4$, the measurement light L converted into the circularly polarized light becomes circularly polarized light beams of opposite rotation directions. Next, the measurement light L converted into the circularly polarized light beams is converted into linearly polarized light beams when the measurement light L passes through the downstream ¼ wavelength plate 22. Specifically, if the measurement light L passes through the downstream ¼ wavelength plate 22 in a state of being the circularly polarized light beams of the opposite rotation directions when the retardation of the photoelastic modulator 20 is $\pm\lambda/4$, the measurement light L becomes linearly polarized light beams of the directions along the X-axis direction and the Y-axis direction to be the arrangement directions of the plurality of groove portions 6a of the photodiode 3.

As described above, the measurement light L emitted from the light source device 2 is converted such that states in which the measurement light L passes through the optical system 30A and becomes the linearly polarized light beams of the two orthogonal directions are repeated in conjunction with the frequency of the voltage change in the AC power supply 19. At this time, the two orthogonal directions of the linearly polarized light beams of the measurement light L having passed through the optical system 30A are adjusted to correspond to the two orthogonal arrangement directions (the X-axis direction and the Y-axis direction) of the plurality of groove portions 6a in the diffraction grating portion 6 of the photodiode 3.

Next, an operation of the photodiode 3 when the measurement light L is incident on the photodiode 3 will be described.

As described above, in the refractive index measuring device 1A, the grating pitch P and the incidence angle α are set such that the quantum efficiencies with respect to the measurement light L of the linearly polarized light beams of the two orthogonal directions of the X-axis direction and the Y-axis direction are equalized with respect to the reference refractive index $n_0$, at the wavelength of the measurement light L (refer to FIG. 6). In addition, the optical system 30A is adjusted such that the measurement light L repeats the linearly polarized light beams of the directions along the two orthogonal arrangement directions (the X-axis direction and the Y-axis direction) of the plurality of groove portions 6a in the diffraction grating portion 6. In this state, when the measurement light L is radiated to the diffraction grating portion 6, the electric signals output from the photodiode 3 become almost constant even if the directions of the linearly polarized light beams of the measurement light L are periodically converted. The reference refractive index $n_0$ may be the refractive index n in a state in which a specific substance is disposed in the diffraction grating portion 6 or may be the refractive index n in a state in which nothing is disposed in the diffraction grating portion 6.

Therefore, when the measured object M having the refractive index n is disposed in the diffraction grating portion 6 (that is, the refractive index n has a value other than the reference refractive index $n_0$), the spectral characteristic of the quantum efficiency changes. There is a predetermined relation between the shift amount of the peak wavelength $\lambda p$ and the refractive index n and there is a predetermined relation between the decrease amount of the peak value and the refractive index n. As a result, an electric signal having information regarding the refractive index n can be obtained by using the shift amount of the peak wavelength $\lambda p$ or the decrease amount of the peak value.

Figure 11:
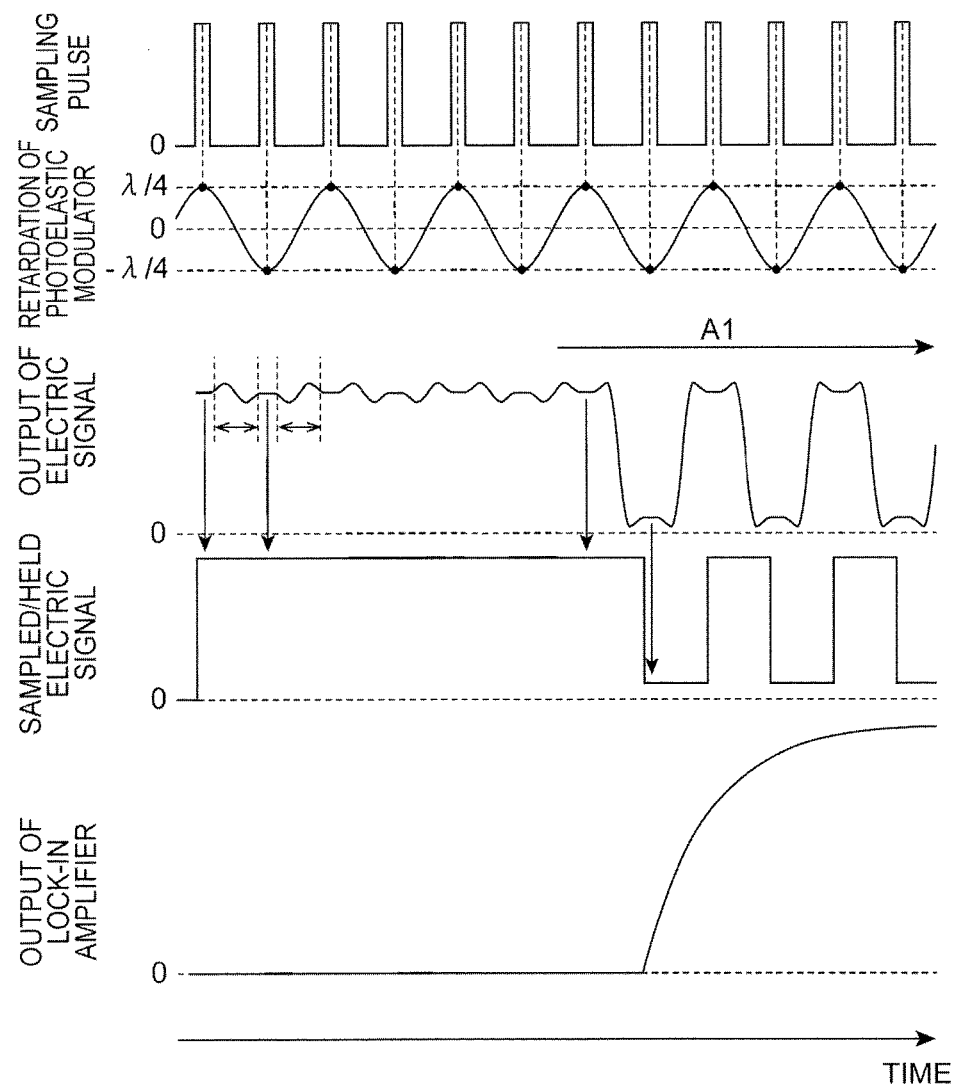
FIG. 11 is a timing chart showing an operation of the refractive index measuring device according to the first embodiment.

Next, processing and detection of the electric signal output from the photodiode 3 will be described. FIG. 11 is a timing chart showing the operation of the refractive index measuring device according to the first embodiment.

The polarization state of the measurement light L is converted from linear polarization to circular polarization in the photoelastic modulator 20. However, the measurement light L is in a state of circularly polarized light only when the retardation of the photoelastic modulator 20 is $\pm \lambda/4$. In this transient period, the measurement light L is in a state of elliptically polarized light. For this reason, unnecessary signals are mixed in the electric signals output from the photodiode 3 in the transient period, which results in becoming one cause of deterioration of the measurement accuracy of the refractive index.

FIG. 11 shows an operation of the refractive index measuring device 1A in the case in which the measured object M having the refractive index n different from the reference refractive index $n_0$ is disposed in the diffraction grating portion 6 in a period shown by an arrow A1 in time shown by a horizontal axis. Electric signals sampled/held before the measured object M is disposed in the diffraction grating portion 6 are kept constant at a relatively high value. Meanwhile, in electric signals sampled/held after the measured object M is disposed, an output of an electric signal sampled in synchronization with the sampling pulse generated at the timing when the retardation of the photoelastic modulator 20 becomes $+\lambda/4$ is kept constant at a relative high value. In addition, an output of an electric signal sampled in synchronization with the sampling pulse generated at the timing when the retardation of the photoelastic modulator 20 becomes $-\lambda/4$ is kept constant at a relatively low value. As such, because the output of the electric signal is kept constant over a necessary period by providing the sample/hold circuit 14, unnecessary signals mixed in the electric signals output from the photodiode 3 are removed.

As described above, after the electric signal output from the photodiode 3 is input to the logarithmic conversion circuit 15 and is logarithmically converted, the electric signal may be input to the sample/hold circuit 14. The output of the sample/hold circuit 14 is input to the signal detection unit 16 and is lock-in detected. Then, the difference of the quantum efficiencies according to the difference of the refractive index n and the reference refractive index $n_0$ is evaluated in the refractive index calculation unit 17, on the basis of the electric signal lock-in detected in the signal detection unit 16, so that the refractive index n of the measured object M is calculated.

By this configuration, the refractive index measuring device 1A according to the first embodiment has the following advantages. That is, because the downstream ¼ wavelength plate 22 is disposed on the downstream of the optical path of the measurement light L of the photoelastic modulator 20, at the time of adjustment of the optical system 30A, the photoelastic modulator 20 having a large size and weight does not need to be moved and time and effort for the adjustment are alleviated. In addition, because the electric signals are sampled in a state in which the retardation of the photoelastic modulator 20 becomes $\pm\lambda/4$ and staying times in this state are the same, the detection of the electric signals in the signal detection unit 16 can be easily performed. In addition, because the staying times in this state are relatively long, time for sampling the electric signals can be secured relatively long and a signal-to-noise (S/N) ratio can be suppressed from decreasing. When the intensity of the unnecessary signals in the transient period is small, the sample/hold circuit 14 can be removed.

As described above, the refractive index measuring device 1A according to the first embodiment includes the semiconductor layers 9, 11, and 12 and the gate insulating layer 13 that are provided on the buried insulating layer 8 formed on the semiconductor silicon substrate 7. In addition, in the refractive index measuring device 1A, the measurement light L emitted from the light source device 2 is guided by the optical system 30A and is incident on the photodiode 3 having the diffraction grating portion 6 in which the plurality of groove portions 6a are formed in the two-dimensional lattice shape, on the gate insulating layer 13. Here, the measurement light L emitted from the light source device 2 is in a state of being the linearly polarized light having the predetermined wavelength and the measurement light L incident on the photodiode 3 is converted at a predetermined frequency by the photoelastic modulator 20 included in the optical system 30A, such that states in which the measurement light L becomes the linearly polarized light beams of the two orthogonal directions are repeated. In addition, the measurement light L of the linearly polarized light beams of the two orthogonal directions are repeatedly incident on the diffraction grating portion 6 in which the plurality of groove portions 6a are formed in the two-dimensional lattice shape and each electric signal of the photodiode 3 in states in which the measurement light L becomes the linearly polarized light beam of each direction is detected. As a result, when the measured object M is disposed on the diffraction grating portion 6, the refractive index n of the measured object M can be obtained on the basis of each electric signal. By this configuration, because the refractive index n can be measured without using a separate light detector, the device configuration can be simplified. In addition, the use efficiency of the measurement light L incident on the photodiode 3 is improved, so that the detection accuracy of the intensity of the measurement light L is improved. In addition, the measurement light L is incident on the same measured object M from the same light source device 2 and optical system 30A and the measurement light L is converted into the electric signal by the same diffraction grating portion 6 and photodiode 3, so that an error is suppressed from occurring in the electric signal. In addition, the electric signal is lock-in detected in the signal detection unit 16, so that the signal-to-noise (S/N) ratio is improved. As a result, the measurement accuracy of the refractive index n of the measured object M can be improved.

Because the refractive index measuring device 1A further includes the refractive index calculation unit 17 to calculate the refractive index n on the basis of the lock-in detected electric signal, the above functions and effects can be suitably realized.

In addition, in the diffraction grating portion 6, the grating pitch P of the plurality of groove portions 6a formed in the two-dimensional lattice shape and the incidence angle α of the measurement light L with respect to the diffraction grating portion 6 are set such that the electric signals with respect to the linearly polarized light beams of the two orthogonal directions are equalized with respect to the predetermined reference refractive index $n_0$. The signal detection unit 16 performs the lock-in detection on the electric signal at the time when the measurement light L becomes the linearly polarized light beams of the directions along the two orthogonal arrangement directions (the X-axis direction and the Y-axis direction) of the plurality of groove portions 6a formed in the two-dimensional lattice shape. As a result, because the lock-in detected output becomes zero at the reference refractive index $n_0$, an amplification factor of the lock-in detection can be increased. Therefore, the intensity of the electric signal corresponding to the refractive index change from the reference refractive index $n_0$ increases, so that the measurement accuracy of the refractive index n can be improved.

Because the optical system 30A includes the downstream ¼ wavelength plate 22 between the photoelastic modulator 20 and the photodiode 3, the optical system 30A can correspond to various configurations of optical systems including other embodiments to be described below.

The refractive index measuring device 1A further includes the logarithmic conversion circuit 15 logarithmically converting the electric signals, at the rear step of the photodiode 3. Evaluating the difference of the logarithmically converted electric signals corresponds to evaluating logarithmic conversion of the ratio of the electric signals. For this reason, the logarithmic conversion circuit 15 is included, so that the refractive index measuring device is hardly affected by the change in the intensity of the measurement light L from the light source device 2. Therefore, the measurement accuracy of the refractive index n can be improved by evaluating the difference of the logarithmically converted electric signals.

The diffraction grating portion 6 further includes the sample/hold circuit 14 to sample/hold the electric signal at each time when the measurement light becomes the linearly polarized light beams of the directions along the two orthogonal arrangement directions (the X-axis direction and the Y-axis direction) of the plurality of groove portions 6a formed in the two-dimensional lattice shape, at the front step of the signal detection unit 16. Therefore, because it is possible to remove the change in the electric signal generated in the transient period when the polarization state of the light is modulated by the photoelastic modulator 20, the measurement accuracy of the refractive index n can be improved.

Here, it is described below that the refractive index measuring device 1A is also useful in a field of biotechnology. Conventionally, as a method of detecting biochemical substances, a method of detecting color development or fluorescence by enzymes and a method of measuring a refractive index are known. Examples of the method of detecting the color development or the fluorescence by the enzymes include enzyme-linked immunosorbent assay (ELISA) and chemiluminescent enzyme immunoassay (CLEIA). Meanwhile, examples of the method of measuring the refractive index include surface plasmon resonance (SPR) which is also used for the refractive index measuring device 1A.

For these methods, for example, in Sandeep Kumar Vashist, et al. "Comparative study of the developed chemiluminescent, ELISA and SPR immunoassay formats for the highly sensitive detection of human albumin", Procedia Chemistry, 2012, No. 6, p. 184-193, the following contents are described with respect to detection of human albumin becoming a marker of diseases and inflammations of a kidney, a liver, and the like. That is, detection sensitivity of the human albumin is high in the order of CLEIA, ELISA, and SPR. However, according to SPR, it is described that quick real-time measurement is enabled, it is not necessary to label an antibody with an enzyme or a fluorescent substance, and kinetics concerning intermolecular interaction and affinity can be analyzed.

In addition, for example, in S. R. Edupuganti, et al. "Biological and synthetic binders for immunoassay and sensor-based detection: generation and characterization of an anti-$AFB_2$ single-chain variable fragment (scFv)", World Mycotoxin Journal, August 2013, No. 6 (3), p. 273-280, the following contents are described with respect to detection of aflatoxin (mold fungus) contained in foods and the like. That is, it is described that detection sensitivity of the aflatoxin is 10 times higher in SPR than in ELISA. This result seems to indicate that SPR can be more sensitive to detection of molecules which cannot be labeled efficiently like the aflatoxin, as compared with ELISA.

As described above, a refractive index measuring device applicable to even the case in which it is not possible to efficiently label molecules to be detected or in the case in which a property of the molecules to be detected is changed by labeling is required in the field of biotechnology.

Here, because the refractive index measuring device 1A according to this embodiment does not need to label the molecules to be detected, the refractive index measuring device 1A is also applicable to the case described above. Therefore, the refractive index measuring device 1A has high utility even in the field of the biotechnology.

[Second Embodiment]

Figure 12:
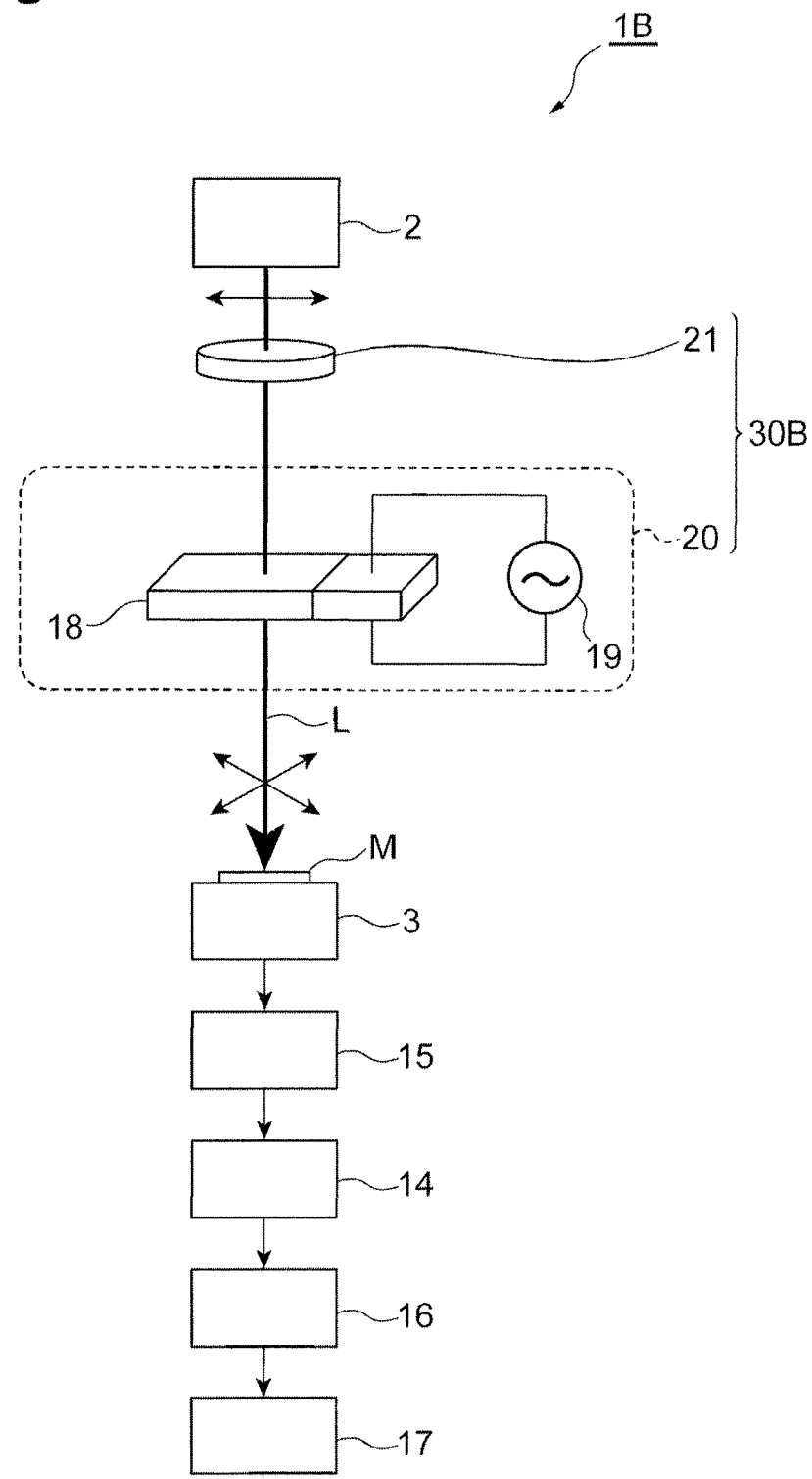
FIG. 12 is a schematic configuration diagram showing a refractive index measuring device according to a second embodiment.
Figure 13:
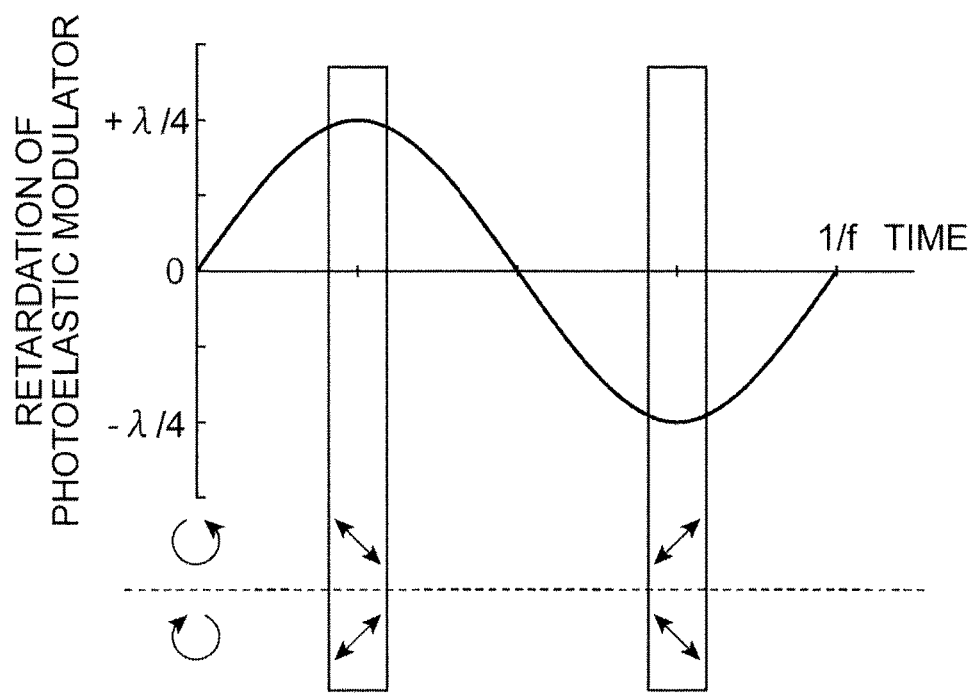
FIG. 13 is a diagram showing a temporal change of a polarization state after conversion by a photoelastic modulator in the second embodiment.

FIG. 12 is a schematic configuration diagram showing a refractive index measuring device according to a second embodiment and FIG. 13 is a diagram showing a temporal change of a polarization state after conversion by a photoelastic modulator according to the second embodiment. A refractive index measuring device 1B according to the second embodiment is different from the refractive index measuring device 1A according to the first embodiment in that the refractive index measuring device 1B includes an optical system 30B having a different configuration.

That is, as shown in FIG. 12, the optical system 30B includes an upstream ¼ wavelength plate (¼ wavelength plate) 21 and a photoelastic modulator 20. Measurement light L emitted from a light source device 2 passes through the upstream ¼ wavelength plate (¼ wavelength plate) 21 and a photoelastic modulation element 18 of the photoelastic modulator 20 in this order and is incident on a photodiode 3.

Similar to a downstream ¼ wavelength plate 22, the upstream ¼ wavelength plate 21 is made of a ¼ wavelength plate. The upstream ¼ wavelength plate 21 generates a phase difference of λ/4 according to a polarization direction of the measurement light L passing through the upstream ¼ wavelength plate 21 and can perform mutual conversion between linearly polarized light and circularly polarized light, for example.

As shown in FIG. 13, in the refractive index measuring device 1B, the measurement light L of the linearly polarized light emitted from the light source device 2 is converted into circularly polarized light when the measurement light L passes through the upstream ¼ wavelength plate 21. At this time, a rotation direction of the circularly polarized light is set by a rotation angle of the upstream ¼ wavelength plate 21. Next, the measurement light L converted into the circularly polarized light is converted into linearly polarized light when the measurement light L passes through the photoelastic modulator 20. Specifically, a maximum retardation of the photoelastic modulator 20 is set to $\lambda/4$. When the retardation of the photoelastic modulator 20 is $\pm\lambda/4$, the measurement light L converted into the circularly polarized light becomes linearly polarized light beams of directions deviated by ±45 degrees with respect to a fast axis and a slow axis of the photoelastic modulator 20.

As described above, the measurement light L emitted from the light source device 2 is converted such that states in which the measurement light L passes through the optical system 30B and becomes linearly polarized light beams of two orthogonal directions are repeated in conjunction with a frequency of a voltage change in an AC power supply 19. At this time, the two orthogonal directions of the linearly polarized light beams of the measurement light L having passed through the optical system 30B are adjusted to correspond to two orthogonal arrangement directions (an X-axis direction and a Y-axis direction) of a plurality of groove portions 6a in a diffraction grating portion 6 of the photodiode 3.

By this configuration, the refractive index measuring device 1B according to the second embodiment has the following advantages. That is, because electric signals are sampled in a state in which the retardation of the photoelastic modulator 20 becomes $\pm\lambda/4$ and staying times in this state are the same, detection of the electric signals in a signal detection unit 16 can be easily performed. In addition, because the staying times in this state are relatively long, time for sampling the electric signals can be secured relatively long and a signal-to-noise (S/N) ratio can be suppressed from decreasing. When the intensity of unnecessary signals in a transient period is small, a sample/hold circuit 14 can be removed.

[Third Embodiment]

Figure 14:
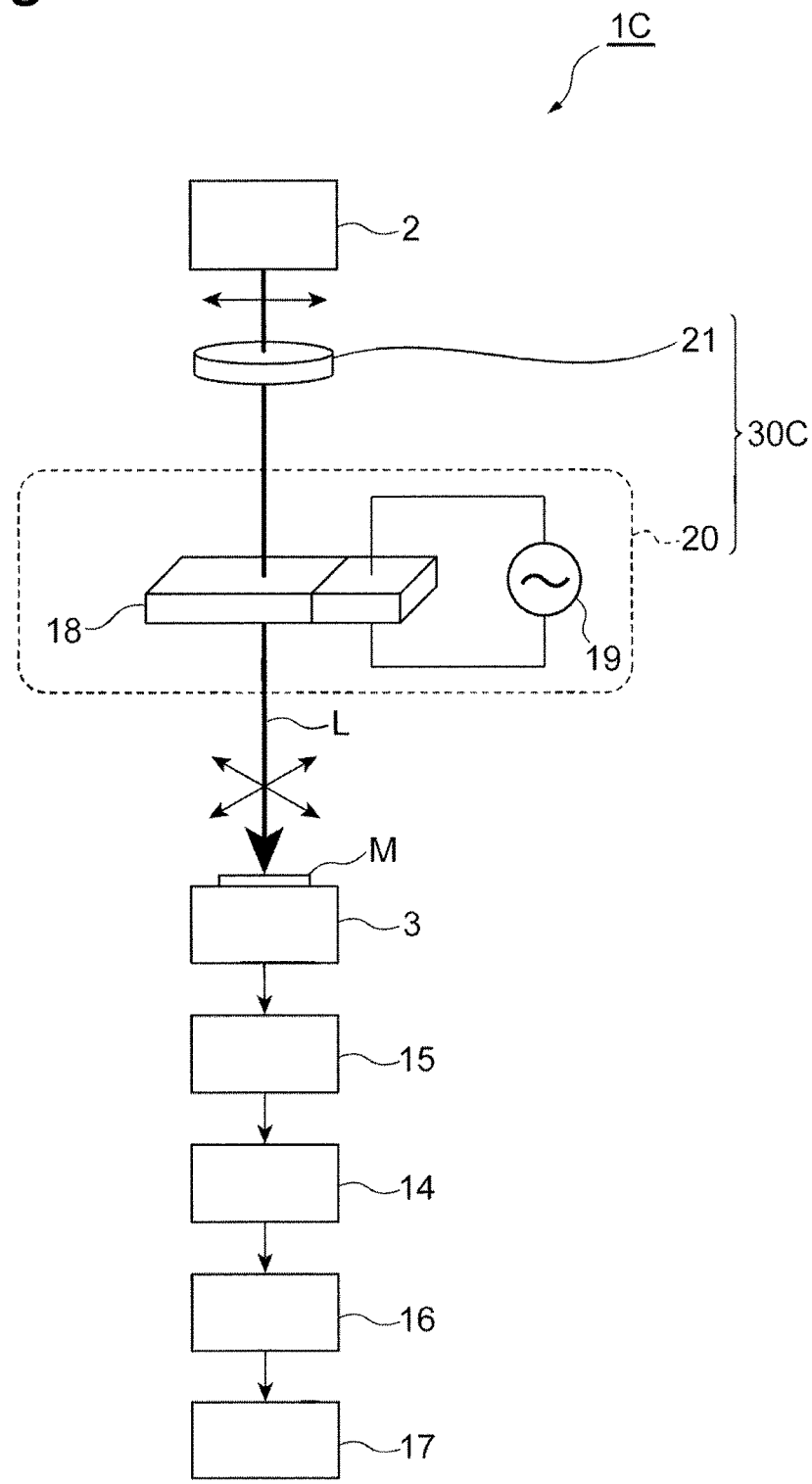
FIG. 14 is a schematic configuration diagram showing a refractive index measuring device according to a third embodiment.
Figure 15:
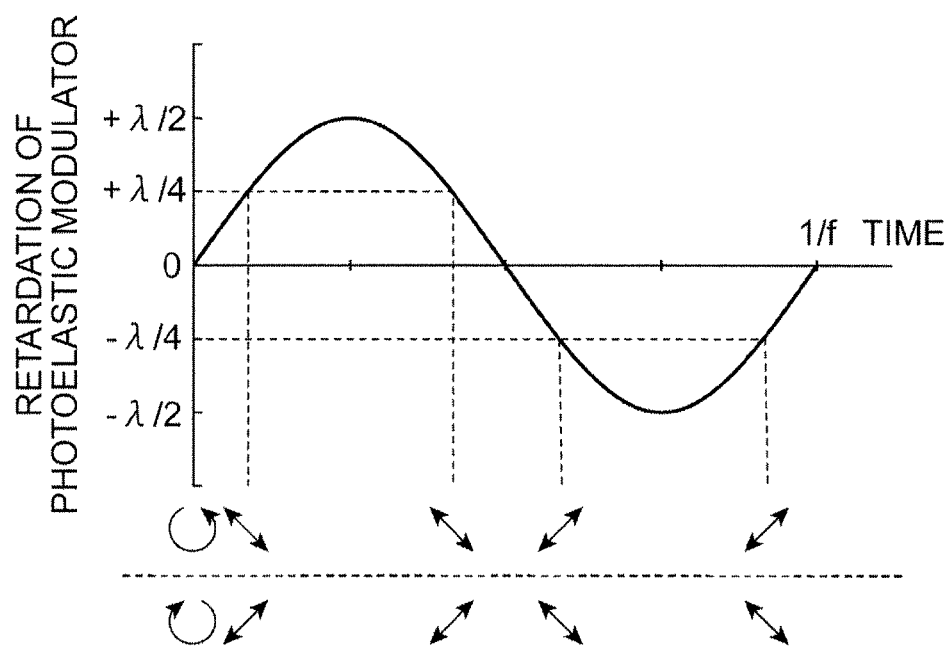
FIG. 15 is a diagram showing a temporal change of a polarization state after conversion by a photoelastic modulator in the third embodiment.

FIG. 14 is a schematic configuration diagram showing a refractive index measuring device according to a third embodiment and FIG. 15 is a diagram showing a temporal change of a polarization state after conversion by a photoelastic modulator according to the third embodiment. A refractive index measuring device 1C according to the third embodiment is different from the refractive index measuring device 1A according to the first embodiment in that the refractive index measuring device 1C includes an optical system 30C having a different configuration.

That is, as shown in FIG. 14, the optical system 30C includes an upstream ¼ wavelength plate (¼ wavelength plate) 21 and a photoelastic modulator 20. Measurement light L emitted from a light source device 2 passes through the upstream ¼ wavelength plate (¼ wavelength plate) 21 and a photoelastic modulation element 18 of the photoelastic modulator 20 in this order and is incident on a photodiode 3.

As shown in FIG. 15, in the refractive index measuring device 1C, the measurement light L of linearly polarized light emitted from the light source device 2 is converted into circularly polarized light when the measurement light L passes through the upstream ¼ wavelength plate 21. At this time, a rotation direction of the circularly polarized light is set by a rotation angle of the upstream ¼ wavelength plate 21. Next, the measurement light L converted into the circularly polarized light is converted into linearly polarized light when the measurement light L passes through the photoelastic modulator 20. Specifically, a maximum retardation of the photoelastic modulator 20 is set to $\lambda/2$. When the retardation of the photoelastic modulator 20 becomes $\pm\lambda/4$ transiently, the measurement light L converted into the circularly polarized light becomes linearly polarized light beams of directions deviated by ±45 degrees with respect to a fast axis and a slow axis of the photoelastic modulator 20.

As described above, the measurement light L emitted from the light source device 2 is converted such that states in which the measurement light L passes through the optical system 30C and becomes linearly polarized light beams of two orthogonal directions are repeated in conjunction with a frequency of a voltage change in an AC power supply 19. At this time, the two orthogonal directions of the linearly polarized light beams of the measurement light L having passed through the optical system 30C are adjusted to correspond to two orthogonal arrangement directions (an X-axis direction and a Y-axis direction) of a plurality of groove portions 6a in a diffraction grating portion 6 of the photodiode 3.

By this configuration, the refractive index measuring device 1C according to the third embodiment has the following advantages. That is, because electric signals are sampled in a state in which the retardation of the photoelastic modulator 20 becomes $\pm\lambda/4$ and staying times in this state are the same, detection of the electric signals in a signal detection unit 16 can be easily performed.

[Fourth Embodiment]

Figure 16:
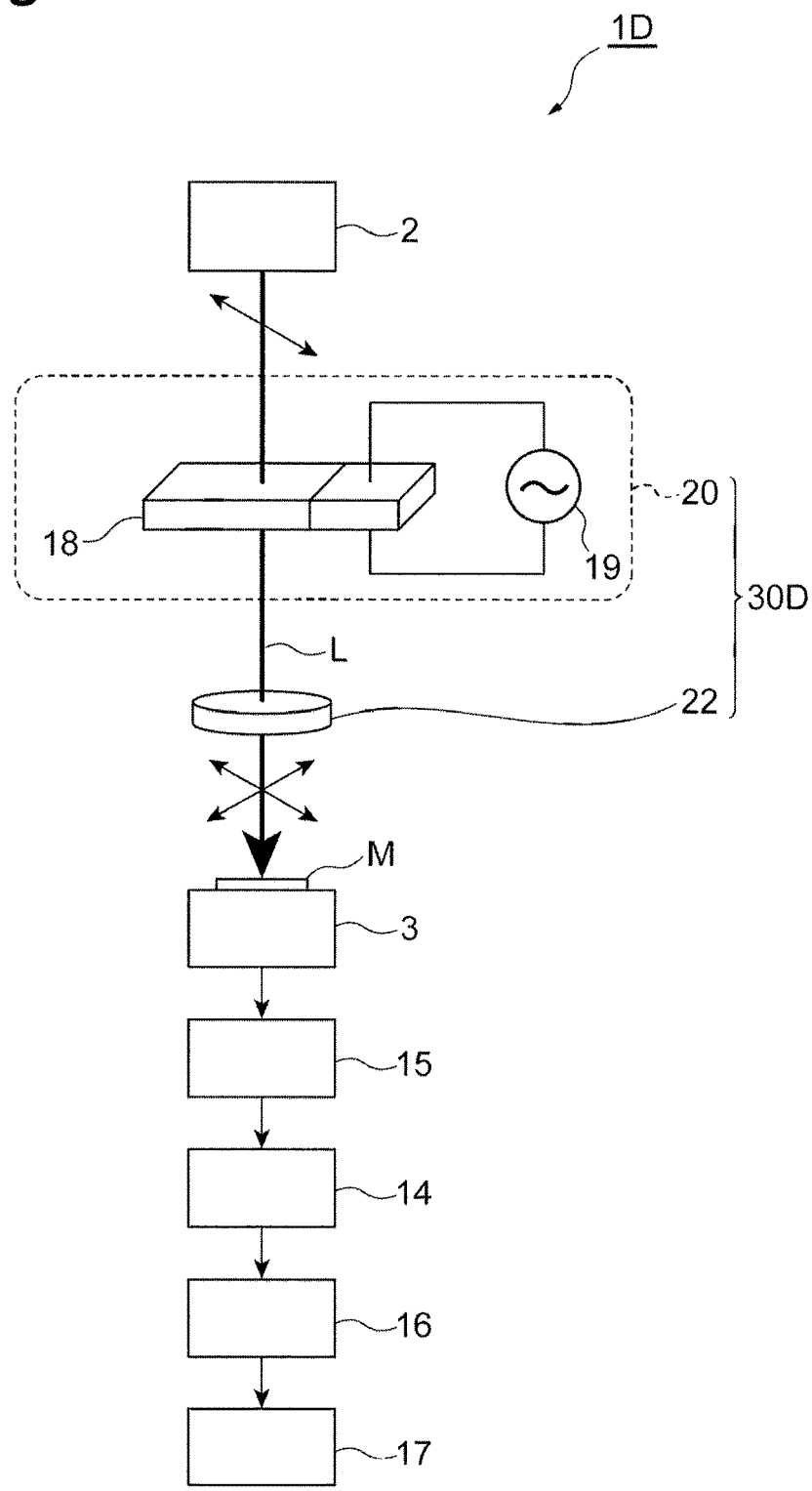
FIG. 16 is a schematic configuration diagram showing a refractive index measuring device according to a fourth embodiment.
Figure 17:
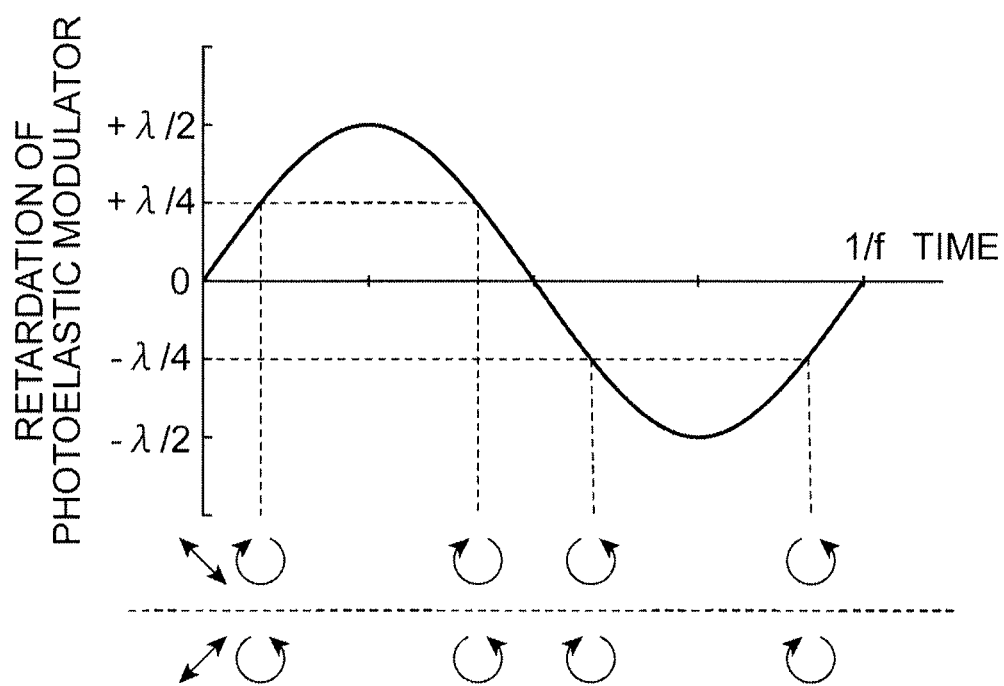
FIG. 17 is a diagram showing a temporal change of a polarization state after conversion by a photoelastic modulator in the fourth embodiment.

FIG. 16 is a schematic configuration diagram showing a refractive index measuring device according to a fourth embodiment and FIG. 17 is a diagram showing a temporal change of a polarization state after conversion by a photoelastic modulator according to the fourth embodiment. A refractive index measuring device 1D according to the fourth embodiment is different from the refractive index measuring device 1A according to the first embodiment in that the refractive index measuring device 1D includes an optical system 30D having a different configuration.

That is, as shown in FIG. 16, the optical system 30D includes a photoelastic modulator 20 and a downstream ¼ wavelength plate (¼ wavelength plate) 22. Measurement light L emitted from a light source device 2 passes through a photoelastic modulation element 18 of the photoelastic modulator 20 and the downstream ¼ wavelength plate 22 in this order and is incident on a photodiode 3.

As shown in FIG. 17, in the refractive index measuring device 1D, the measurement light L emitted from the light source device 2 is linearly polarized light beams of directions deviated by ±45 degrees with respect to a fast axis and a slow axis of the photoelastic modulator 20. The measurement light L is converted into circularly polarized light when the measurement light L passes through the photoelastic modulator 20. A maximum retardation of the photoelastic modulator 20 is set to $\lambda/2$. The measurement light L converted into the circularly polarized light becomes circularly polarized light beams of opposite rotation directions, when the retardation of the photoelastic modulator 20 is $\pm\lambda/4$. Next, the measurement light L converted into the circularly polarized light is converted into linearly polarized light when the measurement light L passes through the downstream ¼ wavelength plate 22. Specifically, if the measurement light L passes through the downstream ¼ wavelength plate 22 in a state of being the circularly polarized light beams of the opposite rotation directions when the retardation of the photoelastic modulator 20 is ±λ/4, the measurement light L becomes linearly polarized light beams of directions along an X-axis direction and a Y-axis direction to be arrangement directions of a plurality of groove portions 6a of the photodiode 3.

As described above, the measurement light L emitted from the light source device 2 is converted such that states in which the measurement light L passes through the optical system 30D and becomes linearly polarized light beams of two orthogonal directions are repeated in conjunction with a frequency of a voltage change in an AC power supply 19. At this time, the two orthogonal directions of the linearly polarized light beams of the measurement light L having passed through the optical system 30D are adjusted to correspond to the two orthogonal arrangement directions (the X-axis direction and the Y-axis direction) of the plurality of groove portions 6a in a diffraction grating portion 6 of the photodiode 3.

By this configuration, the refractive index measuring device 1D according to the fourth embodiment has the following advantages. That is, because the downstream ¼ wavelength plate 22 is disposed on the downstream of an optical path of the measurement light L of the photoelastic modulator 20, at the time of adjustment of the optical system 30D, the photoelastic modulator 20 having a large size and weight does not need to be moved and time and effort for the adjustment are alleviated. In addition, because the electric signals are sampled in a state in which the retardation of the photoelastic modulator 20 becomes ±λ/4 and staying times in this state are the same, detection of the electric signals in a signal detection unit 16 can be easily performed.

[Fifth Embodiment]

Figure 18:
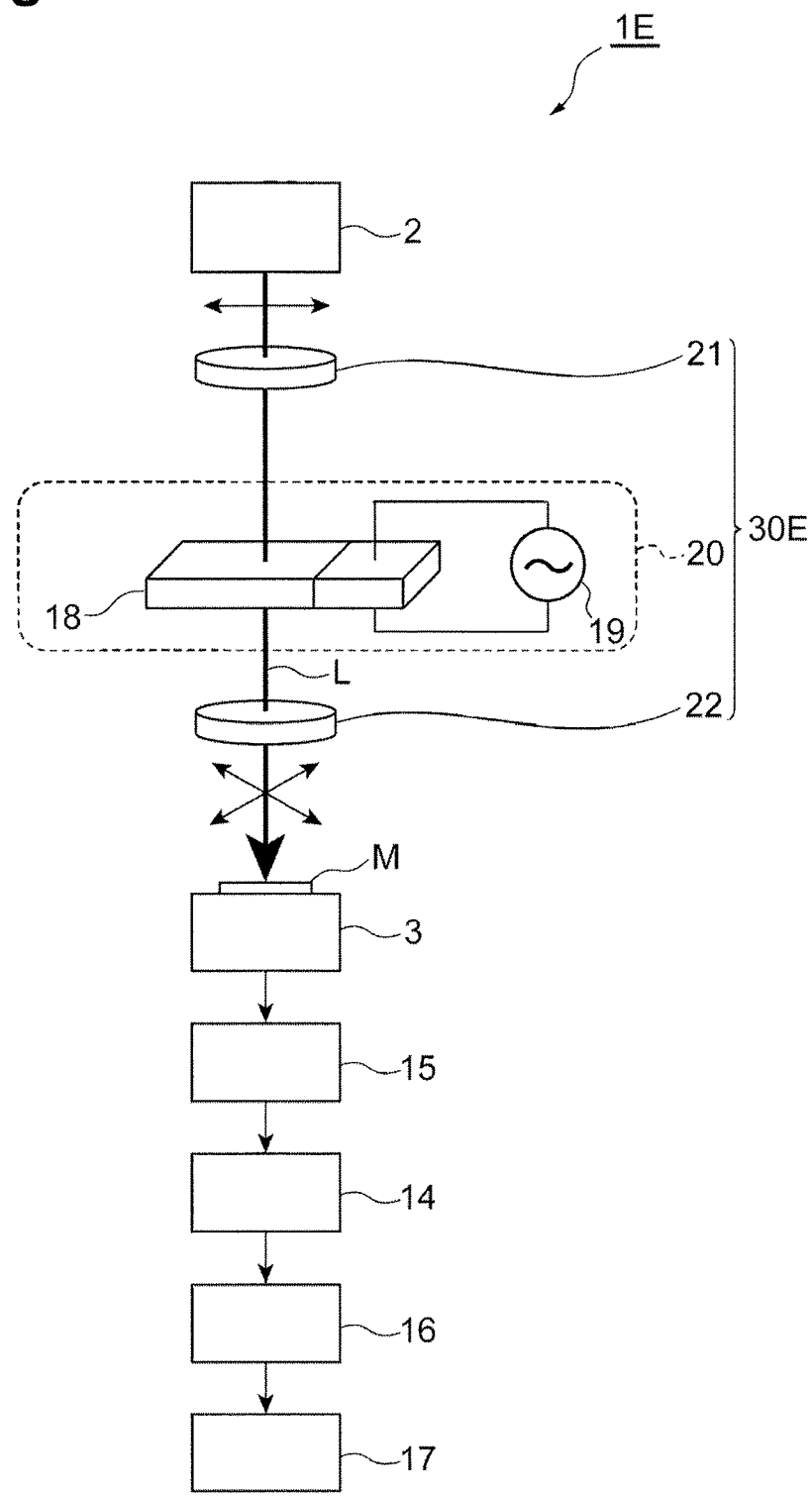
FIG. 18 is a schematic configuration diagram showing a refractive index measuring device according to a fifth embodiment.
Figure 19:
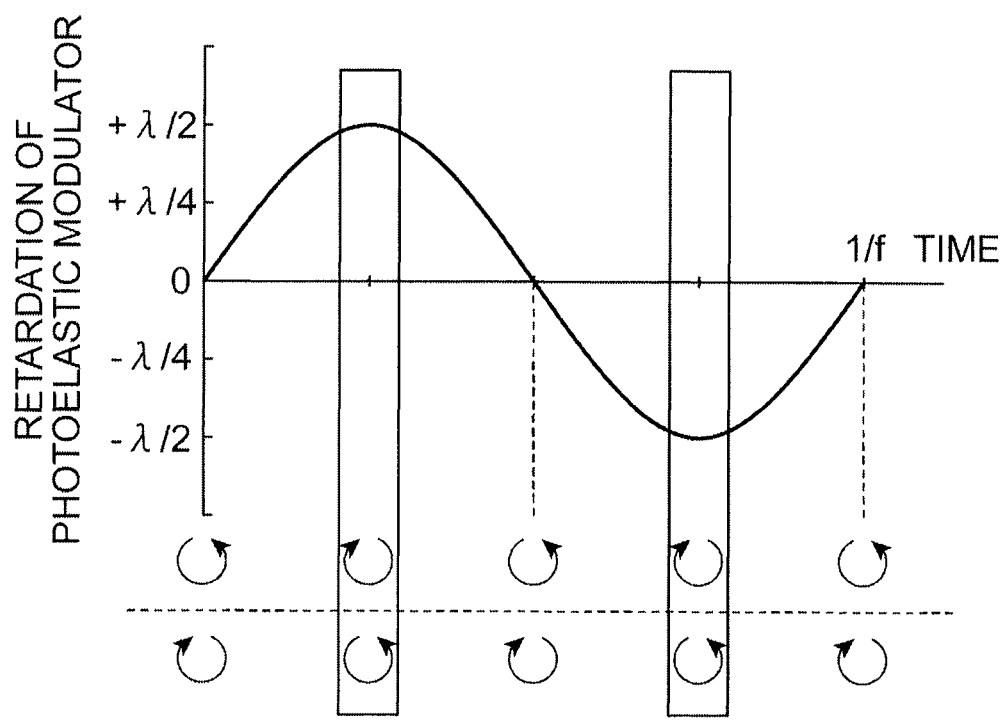
FIG. 19 is a diagram showing a temporal change of a polarization state after conversion by a photoelastic modulator in the fifth embodiment.

FIG. 18 is a schematic configuration diagram showing a refractive index measuring device according to a fifth embodiment and FIG. 19 is a diagram showing a temporal change of a polarization state after conversion by a photoelastic modulator according to the fifth embodiment. A refractive index measuring device 1E according to the fifth embodiment is different from the refractive index measuring device 1A according to the first embodiment in that the refractive index measuring device 1E includes an optical system 30E having a different configuration.

That is, as shown in FIG. 18, the optical system 30E includes an upstream ¼ wavelength plate (¼ wavelength plate) 21, a photoelastic modulator 20, and a downstream ¼ wavelength plate (¼ wavelength plate) 22. Measurement light L emitted from a light source device 2 passes through the upstream ¼ wavelength plate (¼ wavelength plate) 21, a photoelastic modulation element 18 of the photoelastic modulator 20, and the downstream ¼ wavelength plate 22 in this order and is incident on a photodiode 3.

As shown in FIG. 19, in the refractive index measuring device 1E, the measurement light L of linearly polarized light emitted from the light source device 2 is converted into circularly polarized light when the measurement light L passes through the upstream ¼ wavelength plate 21. At this time, a rotation direction of the circularly polarized light can be set by a rotation angle of the upstream ¼ wavelength plate 21. Next, the measurement light L converted into the circularly polarized light is converted into linearly polarized light of a different state when the measurement light L passes through the photoelastic modulator 20. Specifically, a maximum retardation of the photoelastic modulator 20 is set to λ/2. The measurement light L converted into the circularly polarized light is in a state of being circularly polarized light beams of opposite rotation directions, when the retardation of the photoelastic modulator 20 becomes 0 or ±λ/2. Next, the measurement light L having passed through the photoelastic modulator 20 is converted into linearly polarized light when the measurement light L passes through the downstream ¼ wavelength plate 22. Specifically, if the measurement light L passes through the downstream ¼ wavelength plate 22 in a state of being the circularly polarized light beams of the opposite rotation directions, the measurement light L becomes linearly polarized light beams of directions along an X-axis direction and a Y-axis direction to be arrangement directions of a plurality of groove portions 6a of the photodiode 3.

As described above, the measurement light L emitted from the light source device 2 is converted such that states in which the measurement light L passes through the optical system 30E and becomes linearly polarized light beams of two orthogonal directions are repeated in conjunction with twice a frequency of a voltage change in an AC power supply 19. At this time, the two orthogonal directions of the linearly polarized light beams of the measurement light L having passed through the optical system 30E are adjusted to correspond to the two orthogonal arrangement directions (the X-axis direction and the Y-axis direction) of the plurality of groove portions 6a in a diffraction grating portion 6 of the photodiode 3. An electric signal needs to be sampled in a state in which the retardation of the photoelastic modulator 20 becomes 0 and ±λ/2.

By this configuration, the refractive index measuring device 1E according to the fifth embodiment has the following advantages. That is, because the downstream ¼ wavelength plate 22 is disposed on the downstream of an optical path of the measurement light L of the photoelastic modulator 20, at the time of adjustment of the optical system 30E, the photoelastic modulator 20 having a large size and weight does not need to be moved and time and effort for the adjustment are alleviated. Likewise, because the upstream ¼ wavelength plate 21 is disposed on the downstream of the light source device 2 and the upstream of the photoelastic modulator 20, at the time of the adjustment of the optical system 30E, the light source device 2 does not need to be moved and time and effort for the adjustment are alleviated.

[Sixth Embodiment]

Figure 20:
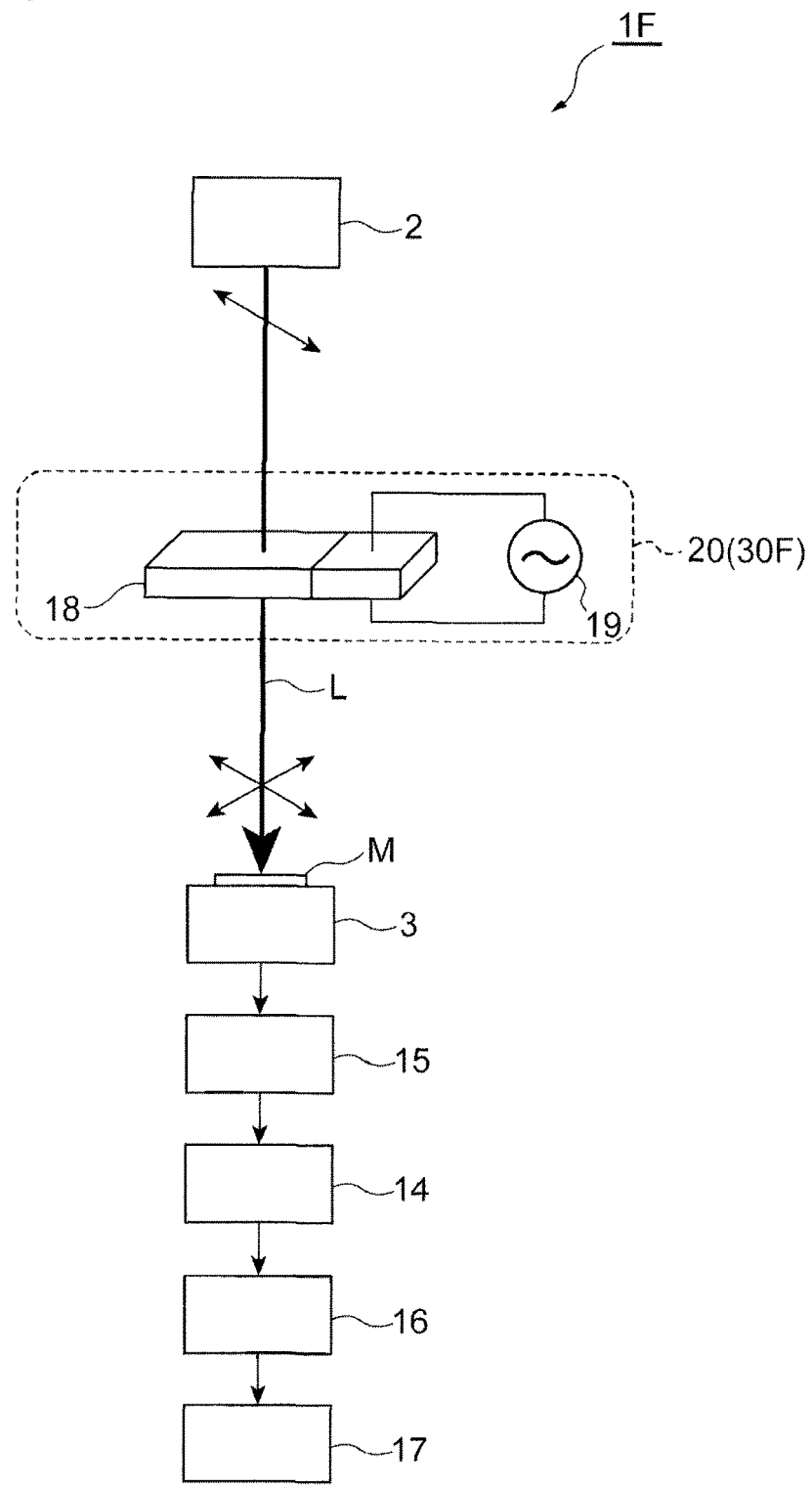
FIG. 20 is a schematic configuration diagram showing a refractive index measuring device according to a sixth embodiment.
Figure 21:
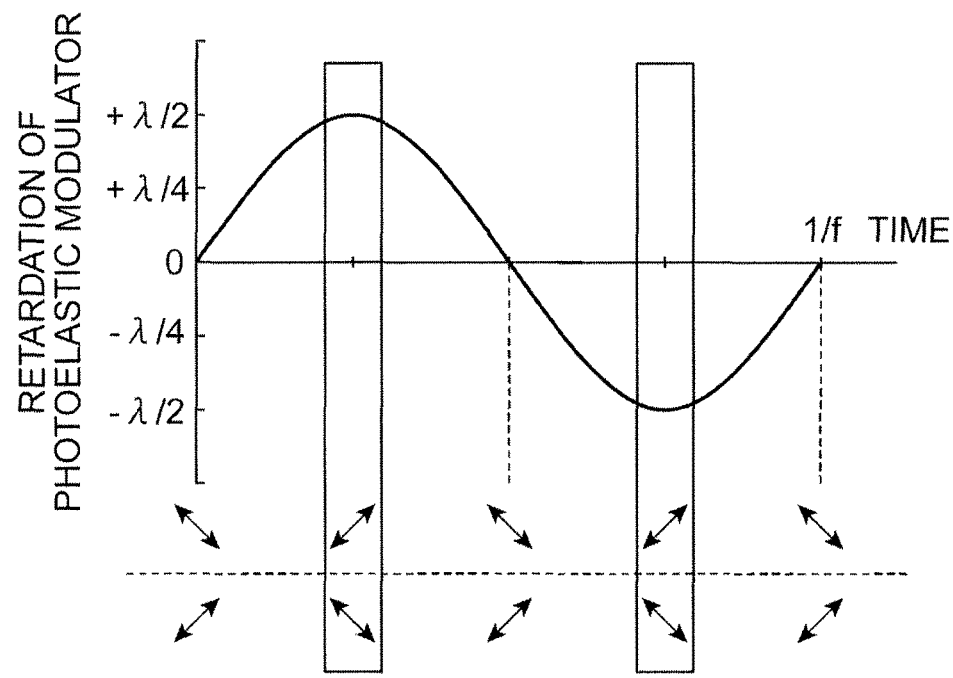
FIG. 21 is a diagram showing a temporal change of a polarization state after conversion by a photoelastic modulator in the sixth embodiment.

FIG. 20 is a schematic configuration diagram showing a refractive index measuring device according to a sixth embodiment and FIG. 21 is a diagram showing a temporal change of a polarization state after conversion by a photoelastic modulator according to the sixth embodiment. A refractive index measuring device 1F according to the sixth embodiment is different from the refractive index measuring device 1A according to the first embodiment in that the refractive index measuring device 1F includes an optical system 30F having a different configuration.

That is, as shown in FIG. 20, the optical system 30F includes a photoelastic modulator 20. Measurement light L emitted from a light source device 2 passes through a photoelastic modulation element 18 of the photoelastic modulator 20 and is incident on a photodiode 3.

As shown in FIG. 21, in the refractive index measuring device 1F, the measurement light L emitted from the light source device 2 is linearly polarized light beams of directions deviated by ±45 degrees with respect to a fast axis and a slow axis of the photoelastic modulator 20. The measurement light L is converted into linearly polarized light of which a direction changes periodically, when the measurement light L passes through the photoelastic modulator 20. Specifically, a maximum retardation of the photoelastic modulator 20 is set to λ/2. The measurement light L becomes the linearly polarized light beams of the directions deviated by ±45 degrees with respect to the fast axis and the slow axis of the photoelastic modulator 20, when the retardation of the photoelastic modulator 20 is 0 or ±λ/2.

As described above, the measurement light L emitted from the light source device 2 is converted such that states in which the measurement light L passes through the optical system 30F and becomes linearly polarized light beams of two orthogonal directions are repeated in conjunction with twice a frequency of a voltage change in an AC power supply 19. At this time, the two orthogonal directions of the linearly polarized light beams of the measurement light L having passed through the optical system 30F are adjusted to correspond to two orthogonal arrangement directions (an X-axis direction and a Y-axis direction) of a plurality of groove portions 6a in a diffraction grating portion 6 of the photodiode 3. An electric signal needs to be sampled in a state in which the retardation of the photoelastic modulator 20 becomes 0 and ±λ/2.

By this configuration, the refractive index measuring device 1F according to the sixth embodiment has the following advantages. That is, because the direction of the linearly polarized light can be adjusted by only the photoelastic modulator 20, a configuration of the optical system 30F can be simplified.

The refractive index measuring device according to the present invention is not limited to the embodiments. For example, in the embodiments, the semiconductor silicon substrate 7 is used in the photodiode 3. However, a substrate made of a metal may be used.

In addition, the plurality of groove portions 6a formed in the diffraction grating portion 6 may not penetrate the surface of the gate insulating layer 13 and may be provided in the inner portion of the gate insulating layer 13.

In addition, if the plurality of groove portions 6a are formed two-dimensionally, any shape can be adopted. That is, the plurality of groove portions 6a may not be formed in the two-dimensional lattice shape and the two arrangement directions of the groove portions formed two-dimensionally may not be orthogonal to each other. For example, the arrangement of the plurality of groove portions 6a may be a rectangular lattice shape, a hexagonal lattice shape, a diagonal lattice shape, a face-centered rectangular lattice shape, or a triangular lattice shape.

Here, the refractive index measuring device may further include the refractive index calculation unit that calculates the refractive index on the basis of the lock-in detected electric signal. In this case, the above functions and effects can be suitably realized.

In addition, in the diffraction grating portion, the groove portions are formed in the two-dimensional lattice shape and the period of the groove portions and the incidence angle of the light with respect to the diffraction grating portion may be set such that the electric signals with respect to the linearly polarized light beams of the two orthogonal directions are equalized with respect to the wavelength of the predetermined light source and the predetermined reference refractive index. The signal detection unit may perform the lock-in detection on the electric signal at the time when the light becomes the linearly polarized light beams of the directions along the two orthogonal arrangement directions of the groove portions formed in the two-dimensional lattice shape. In this case, because the lock-in detected output becomes zero at the reference refractive index, an amplification factor of the lock-in detection can be increased. Therefore, the intensity of the electric signal corresponding to the refractive index change from the reference refractive index increases, so that the measurement accuracy of the refractive index can be improved.

In addition, the optical system may include the ¼ wavelength plate at least between the light source and the photoelastic modulator or between the photoelastic modulator and the photodiode. In this case, a combination of the ¼ wavelength plate and the photoelastic modulator is changed, so that it is possible to cope with various configurations of the optical system.

The refractive index measuring device may further include the logarithmic conversion circuit logarithmically converting the electric signals, at the front step of the signal detection unit. Evaluating the difference of the logarithmically converted electric signals corresponds to evaluating logarithmic conversion of the ratio of the electric signals. For this reason, when the above configuration is adopted, the refractive index measuring device is hardly affected by the change in the intensity of the light from the light source. Therefore, the measurement accuracy of the refractive index can be improved by evaluating the difference of the logarithmically converted electric signals.

In addition, the two arrangement directions of the groove portions formed two-dimensionally may be orthogonal to each other in the diffraction grating portion and the sample/hold circuit to sample/hold the electric signal at each time when the light becomes the linearly polarized light beams of the directions along the arrangement directions may be further included at the front step of the signal detection unit. In this case, because it is possible to remove the change in the electric signal generated in the transient period when the polarization state of the light is modulated by the photoelastic modulator, the measurement accuracy of the refractive index can be improved.

REFERENCE SIGNS LIST 1A to 1F: refractive index measuring device, 2: light source device (light source), 3: photodiode, 6: diffraction grating portion, 6a: groove portion, 7: silicon substrate (substrate), 8: buried insulating layer, 9, 11, 12: semiconductor layer, 13: gate insulating layer, 16: signal detection unit, 20: photoelastic modulator, 30A to 30F: optical system, L: measurement light (light)

The invention claimed is:
1. A refractive index measuring device, comprising:
a photodiode configured to have a substrate made of a semiconductor or a metal, a buried insulating layer formed on the substrate, a semiconductor layer including a p-type semiconductor layer and an n-type semiconductor layer formed to be arranged along a predetermined region on the buried insulating layer, a gate insulating layer formed on the semiconductor layer, and a diffraction grating portion disposed on the gate insulating layer and having groove portions formed two-dimensionally in a planar conductive member;
a light source configured to emit linearly polarized light having a predetermined wavelength;
an optical system configured to include a photoelastic modulator, convert the light such that two states in which the light becomes linearly polarized light beams of two orthogonal directions are alternately repeated at a predetermined frequency, and guide the converted light to the photodiode; and an amplifier configured to perform lock-in detection on electric signals output from the photodiode when the light is incident on the photodiode through the optical system, wherein the lock-in detection comprises detecting a differential voltage of the electrical signals at two timings, at the predetermined frequency, when the light becomes the linearly polarized light beams of the two orthogonal directions, wherein the groove portions are arranged at a predetermined first grating pitch in a first direction and are arranged at a predetermined second grating pitch in a second direction crossing the first direction.

2. The refractive index measuring device according to claim 1, further comprising a refractive index measuring device which is configured to calculate a refractive index based on the electric signals that are lock-in detected by the amplifier and based on a difference in quantum efficiency associated with a reference refractive index.

3. The refractive index measuring device according to claim 2, wherein
two arrangement directions of the groove portions formed two-dimensionally are orthogonal to each other in the diffraction grating portion,
the refractive index measuring device further comprising a sample/hold circuit configured to be provided at a front step of the amplifier and sample/hold the electric signals at each time when the light becomes linearly polarized light beams of directions along the arrangement directions.

4. The refractive index measuring device according to claim 1, wherein
in the diffraction grating portion, the groove portions are formed in a two-dimensional lattice shape and a period of the groove portions and an incidence angle of the light with respect to the diffraction grating portion are set such that the electric signals with respect to the linearly polarized light beams of the two orthogonal directions are equalized with respect to a wavelength of a predetermined light source and a predetermined reference refractive index, and the amplifier performs the lock-in detection on the electric signals at time when the light becomes linearly polarized light beams of directions along two orthogonal arrangement directions of the groove portions formed in the two-dimensional lattice shape.

5. The refractive index measuring device according to claim 1, wherein the optical system includes a ¼ wavelength plate at least between the light source and the photoelastic modulator or between the photoelastic modulator and the photodiode.

6. The refractive index measuring device according to claim 1, further comprising a logarithmic conversion circuit configured to be provided at a rear step of the photodiode and logarithmically convert the electric signals.

7. The refractive index measuring device according to claim 1, wherein the first direction and the second direction are orthogonal to each other.

8. The refractive index measuring device according to claim 1, wherein the first grating pitch and the second grating pitch are equal to each other.

9. The refractive index measuring device according to claim 1, wherein each of the groove portions has an opening of a square shape.

10. The refractive index measuring device according to claim 1, wherein
two arrangement directions of the groove portions formed two-dimensionally are orthogonal to each other in the diffraction grating portion, and
further comprising a refractive index measuring device which is configured to calculate a refractive index based on the electric signals that are lock-in detected by the amplifier and based on a difference in quantum efficiency associated with a reference refractive index,
wherein the refractive index measuring device comprises a sample/hold circuit configured to be provided at a front step of the amplifier and sample/hold the electric signals at each time when the light becomes linearly polarized light beams of directions along the arrangement directions.

* * * * *